(12) United States Patent
Siewerdsen et al.

(10) Patent No.: US 9,218,643 B2
(45) Date of Patent: Dec. 22, 2015

(54) METHOD AND SYSTEM FOR REGISTERING IMAGES

(75) Inventors: Jeffrey H. Siewerdsen, Baltimore, MD (US); Sajendra Nithiananthan, Baltimore, MD (US); Daniel J. Mirota, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 115 days.

(21) Appl. No.: 14/117,009

(22) PCT Filed: May 14, 2012

(86) PCT No.: PCT/US2012/037797
§ 371 (c)(1),
(2), (4) Date: Nov. 11, 2013

(87) PCT Pub. No.: WO2012/155136
PCT Pub. Date: Nov. 15, 2012

(65) Prior Publication Data
US 2014/0079338 A1   Mar. 20, 2014

Related U.S. Application Data

(60) Provisional application No. 61/485,580, filed on May 12, 2011.

(51) Int. Cl.
  *G06T 3/00*    (2006.01)
  *G06T 7/00*    (2006.01)
  (Continued)

(52) U.S. Cl.
  CPC ............. *G06T 3/0068* (2013.01); *G06T 7/0012* (2013.01); *G06T 7/0034* (2013.01);
  (Continued)

(58) Field of Classification Search
  CPC ..... G06T 11/60; G06T 3/0068; G06T 7/0012; G06T 7/0034; G06T 2207/10084; G06T 2207/20016
  USPC ................. 382/284, 294, 278, 291, 131, 293; 600/407, 437
  See application file for complete search history.

(56) References Cited

U.S. PATENT DOCUMENTS

| 6,731,810 B1 * | 5/2004 | Miura et al. .................. 382/236 |
| 7,023,450 B1 * | 4/2006 | Weitbruch et al. ............ 345/593 |

(Continued)

OTHER PUBLICATIONS

Bachar et al., Three-dimensional tomosynthesis and cone-beam computed tomography: an experimental study for fast, low-dose intraoperative imaging technology for guidance of sinus and skull base surgery. Laryngoscope. 2009;119(3):434-441.

(Continued)

*Primary Examiner* — Mekonen Bekele
(74) *Attorney, Agent, or Firm* — Venable LLP; Henry J. Daley

(57) ABSTRACT

A system for registering images includes an image registration unit. The image registration unit is configured to receive first image data for a first image in an N-dimensional space, receive second image data for a second image in the N-dimensional space, calculate a field of update vectors that maps the first image into a moving image, and map the first image into the moving image using the field of update vectors such that the moving image more closely matches the second image. The field of update vectors includes a plurality of N+M dimensional update vectors, each update vector having N spatial components and M extra components. N is a number greater than zero, and M is a number greater than zero. The M extra components of the plurality of update vectors identify portions of the first image that are assigned external values during the mapping the first image into the moving image.

42 Claims, 12 Drawing Sheets

(51) Int. Cl.

| | |
|---|---|
| *G06T 11/60* | (2006.01) |
| *A61B 6/03* | (2006.01) |
| *A61B 6/12* | (2006.01) |
| *A61B 6/00* | (2006.01) |

(52) U.S. Cl.
CPC ............... *G06T 11/60* (2013.01); *A61B 6/032* (2013.01); *A61B 6/12* (2013.01); *A61B 6/4085* (2013.01); *A61B 6/506* (2013.01); *G06T 2207/10084* (2013.01); *G06T 2207/20016* (2013.01)

(56) References Cited

U.S. PATENT DOCUMENTS

| | | | | |
|---|---|---|---|---|
| 7,756,359 | B1* | 7/2010 | Nord et al. | 382/294 |
| 8,295,353 | B2* | 10/2012 | Miyoshi et al. | 375/240.16 |
| 8,369,597 | B2* | 2/2013 | Hyun et al. | 382/131 |
| 2002/0191696 | A1* | 12/2002 | Moni et al. | 375/240.03 |
| 2005/0063468 | A1* | 3/2005 | Shimizu et al. | 375/240.16 |
| 2006/0004275 | A1* | 1/2006 | Vija et al. | 600/407 |
| 2008/0009724 | A1* | 1/2008 | Lee et al. | 600/437 |
| 2008/0080788 | A1* | 4/2008 | Nord et al. | 382/294 |
| 2008/0123927 | A1* | 5/2008 | Miga et al. | 382/131 |
| 2009/0087124 | A1* | 4/2009 | Nord et al. | 382/296 |
| 2009/0304252 | A1* | 12/2009 | Hyun et al. | 382/131 |
| 2010/0226440 | A1* | 9/2010 | Miyoshi et al. | 375/240.16 |

OTHER PUBLICATIONS

Bachar et al., Image quality and localization accuracy in C-arm tomosynthesis-guided head and neck surgery. Med Phys. 2007;34(12):4664-4677.

Balachandran et al., Evaluation of portable CT scanners for otologic image-guided surgery. Int J Comput Assist Radiol Surg. 2012;7(2):315-321.

Chan et al., Cone-beam computed tomography on a mobile C-arm: novel intraoperative imaging technology for guidance of head and neck surgery. J Otolaryngol Head Neck Surg. 2008;37(1):81-90.

Daly et al., Intraoperative cone-beam CT for guidance of head and neck surgery: Assessment of dose and image quality using a C-arm prototype. Med Phys. 2006;33(10):3767-80.

Dawson et al., Advances in image-guided radiation therapy. J. Clin. Oncol. 2007;25(8):938-946.

Jaffray et al., Cone-beam computed tomography with a flat-panel imager: initial performance characterization. Med Phys. 2000;27(6):1311-1323.

Lauritsch et al., Towards cardiac C-arm computed tomography. IEEE Trans Med Imaging. 2006;25(7):922-934.

Miga et al., Modeling of retraction and resection for intraoperative updating of images. Neurosurgery. 2001;49(1):75-84; discussion 84-5.

Nithiananthan et al., Deformable registration for intra-operative cone-beam CT guidance of head and neck surgery. In: Engineering in Medicine and Biology Society, 2008. EMBS 2008. 30th Annual International Conference of the IEEE.; 2008:3634-3637.

Nithiananthan et al., Demons deformable registration for CBCT-guided procedures in the head and neck: Convergence and accuracy. Med. Phys. 2009;36(10):4755-4764.

Nithiananthan et al., Demons Deformable Registration of CT and Cone-Beam CT Using an Iterative Intensity Matching Approach. Medical Physics. 2011.

Pennec et al., Understanding the "Demon's Algorithm": 3D Non-rigid Registration by Gradient Descent. In: Proceedings of the Second International Conference on Medical Image Computing and Computer-Assisted Intervention. Springer-Verlag; 1999:597-605. Available at: http://portal.acm.org/citation.cfm?id=709761. Accessed Apr. 26,2009.

Periaswamy et al., Medical image registration with partial data. Med Image Anal. 2006;10(3):452-464.

Risholm et al., A non-rigid registration framework that accommodates resection and retraction. Inf Process Med Imaging. 2009;21:447458.

Risholm et al., Validation of a nonrigid registration framework that accommodates tissue resection. In: San Diego, California, USA; 2010:762319-762319-11. Available at:; http://link.aip.org/link/P SISDG/v7623/i1/p762319/s1&Agg=doi. Accessed Jan. 24,2011.

Santos et al., The accuracy of intraoperative 0-arm images for the assessment of pedicle screw postion. Spine. 2012;37(2):E119-125.

Schafer et al., Mobile C-arm cone-beam CT for guidance of spine surgery: image quality, radiation dose, and integration with interventional guidance. Med Phys. 2011;38(8):4563-4574.

Sezgin et al., Survey over image thresholding techniques and quantitative performance evaluation. J. Electron. Imaging. 2004;13(1):146-168.

Siewerdsen et al., Cone-beam CT with a flat-panel detector on a mobile C-arm: preclinical investigation in image-guided surgery of the head and neck. In: Medical Imaging 2005: Visualization, Image-Guided Procedures, and Display.vol. 5744. San Diego, CA, USA: SPIE; 2005:789-797. Available at: http ://link.aip org/link/?P SI/5744/789/1. Accessed Feb. 10, 2009.

Thirion J. Fast non-rigid matching of 3D medical images. France: INRIA; 1995. Available at: http://hal.inrialeinria-00077268/en/. Accessed Feb. 12,2009.

Thirion JP. Image matching as a diffusion process: an analogy with Maxwell's demons. Med Image Anal. 1998;2(3):243-260.

Vercauteren et al., Diffeomorphic demons: Efficient non-parametric image registration. Neurolmage. 2009;45(1, Supplement 1):561-572.

Wang et al., Validation of an accelerated "demons" algorithm for deformable image registration in radiation therapy. Phys Med Biol. 2005;50(12):2887-2905.

International Search Report and Written Opinion of PCT/US2012/037797.

* cited by examiner

Moving Image ($I_0$) | Fixed Image ($I_{def+exc}$)
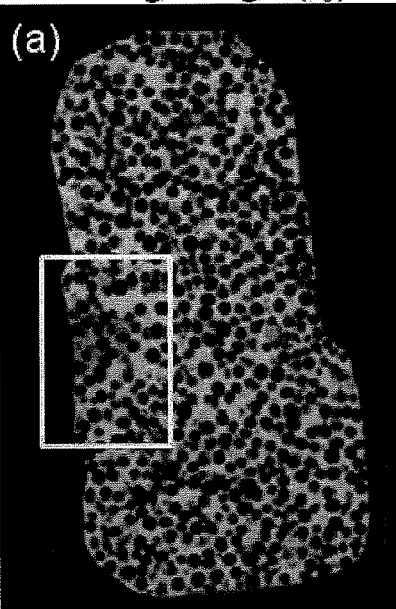 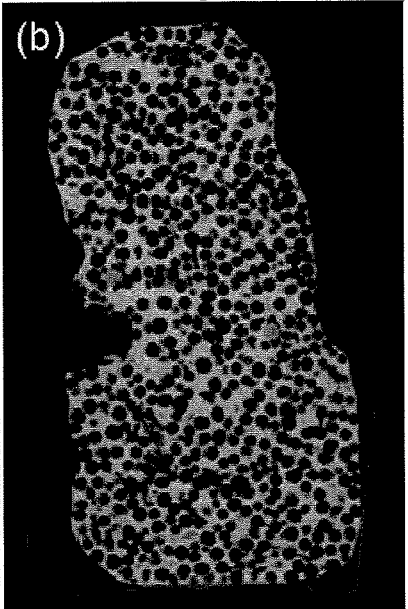
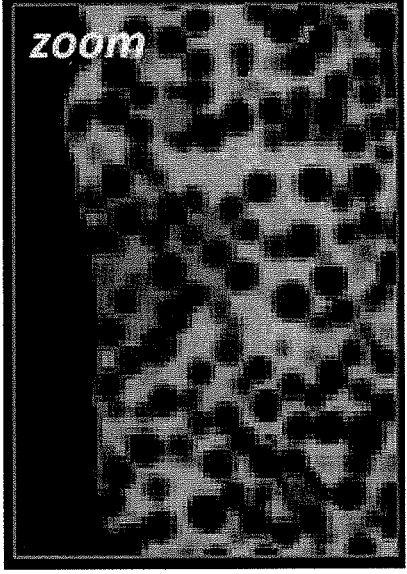 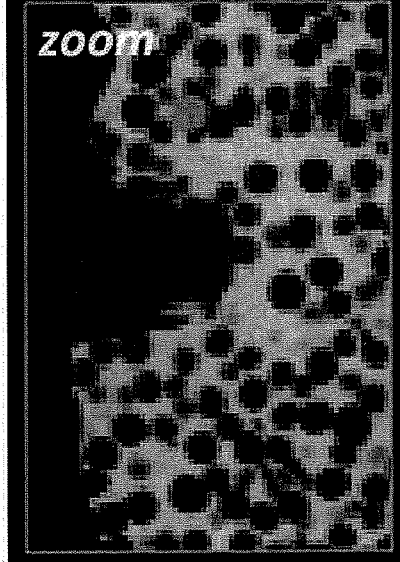
FIG. 5A     FIG. 5B

METHOD AND SYSTEM FOR REGISTERING IMAGES

CROSS-REFERENCE OF RELATED APPLICATION

This is a national stage application under 35 U.S.C. §371 of PCT/US2012/037797 filed May 14, 2012, the entire contents of which are incorporated herein by reference and this application claims priority to U.S. Provisional Application No. 61/485,580 filed May 12, 2011, the entire contents of which are hereby incorporated by reference.

This invention was made with Government support of Grant No. R01-CA-127444, awarded by the Department of Health and Human Services, The National Institutes of Health (NIH). The U.S. Government has certain rights in this invention.

BACKGROUND

1. Field of Invention

The field of the currently claimed embodiments of this invention relates to systems and methods for registering images, and more particularly to systems and methods for registering images in an N dimensional space using N+M dimensions.

2. Discussion of Related Art

Ongoing advances in cone-beam computed tomography (CBCT) enable high-quality 3D imaging for image-guided interventions, including image-guided radiation therapy (IGRT) and image-guided surgery (IGS). The ability to acquire up-to-date images in the course of intervention offers the potential to overcome the limitations of conventional image guidance systems that operate in the context of preoperative data only and fail to account for anatomical change occurring during therapy. Such systems have entered broad application in IGRT,[1] cardiovascular interventions,[2] and high-precision IGS including orthopaedic/spine surgery[3,4] and head and neck/skull base surgery.[5-8]

Key to many of these applications is the ability to register preoperative images (e.g., preoperative CT along with registered MR or PET images) and planning data to intraoperative CBCT. Such registration algorithms must be sufficiently fast and well integrated so as not to impede surgical workflow and provide sufficient geometric accuracy for the particular interventional task. Rigid registration is often insufficient due to variation in patient positioning between preoperative and intraoperative setups as well as anatomical deformations occurring during intervention. In head and neck/skull base surgery (the focus of examples below), despite the largely rigid anatomical context, rigid registration alone fails to account for independent (piecewise-rigid) motion of the neck, jaw, and skull as well as soft-tissue deformations occurring during the procedure—e.g., displacement of sinus contents, herniation of the orbital wall/lamina papyracea, and deformation of the tongue and oropharynx.

These challenges motivated previous work in developing a variant of the Demons registration method[9-13] well suited to CBCT-guided procedures.[14] The method includes: i.) a basic morphological pyramid providing registration within ~20 s; ii.) a "smart" convergence criterion that automatically advances each level of the pyramid to achieve sub-voxel (~0.5 mm) registration accuracy and eliminate extraneous iterations;[15] and iii.) an intensity matching step concurrent with the iterative registration process to provide robustness against image intensity (voxel value) mismatch in CT-to-CBCT or CBCT-to-CBCT registration.[16]

In addition to the basic challenges of tissue deformation in image-guided procedures is a novel and largely unaddressed problem: what if the differences between the preoperative ("moving") image and the intraoperative ("fixed") image involve not only tissue deformation but also the physical removal of mass? In IGRT, an example of a missing tissue problem is weight loss over the course of multiple radiotherapy fractions. In IGS, the problem can be more explicit and includes the physical resection of tissues on surgical approach (e.g., excision of ethmoid air cells on approach to the sphenoid sinus) and removal of the surgical target itself (e.g., drillout of a bony lesion). The behavior of deformable registration algorithms in the presence of missing tissue is an important consideration, since straightforward application of conventional registration approaches may lead to spurious distortion in regions of mismatch—which are often the regions of primary interest (e.g., in proximity to a partially resected surgical target). Registration in the presence of large surgical excisions presents new technical challenges compared to registration in the presence of deformations alone. Similarly, registration in the presence of structures added to the fixed image (e.g., surgical devices) presents a significant challenge. Accordingly, there remains a need for improved systems and methods for registering images.

SUMMARY

A system for registering images according to an embodiment of the current invention includes an image registration unit. The image registration unit is configured to receive first image data for a first image in an N-dimensional space, receive second image data for a second image in the N-dimensional space, calculate a field of update vectors that maps the first image into a moving image, and map the first image into the moving image using the field of update vectors such that the moving image more closely matches the second image. The field of update vectors includes a plurality of N+M dimensional update vectors, each update vector having N spatial components and M extra components. N is a number greater than zero, and M is a number greater than zero. The M extra components of the plurality of update vectors identify portions of the first image that are assigned external values during the mapping the first image into the moving image.

A method of registering images according to an embodiment of the current invention includes receiving first image data for a first image in an N-dimensional space, receiving second image data for a second image in the N-dimensional space, calculating a field of update vectors that maps the first image into a moving image, and mapping the first image into the moving image using the field of update vectors such that the moving image more closely matches the second image. The field of update vectors includes a plurality of N+M dimensional update vectors, each update vector having N spatial components and M extra components. N is an integer greater than zero, and M is an integer greater than zero. The M extra components of the plurality of update vectors identify portions of the first image that are assigned external values during the mapping the first image into the moving image.

A computer-readable medium according to an embodiment of the current invention includes computer-executable code for registering images. The computer-executable code includes instructions that, when executed by the computer, causes the computer to receive first image data for a first image in an N-dimensional space, receive second image data for a second image in the N-dimensional space, calculate a field of update vectors that maps the first image into a moving image, and map the first image into the moving image using the field of update vectors such that the moving image more closely matches the second image. The field of update vectors includes a plurality of N+M dimensional update vectors, each update vector having N spatial components and M extra components. N is an integer greater than zero, and M is an integer greater than zero. The M extra components of the plurality of update vectors identify portions of the first image that are assigned external values during the mapping the first image into the moving image.

BRIEF DESCRIPTION OF THE DRAWINGS

Further objectives and advantages will become apparent from a consideration of the description, drawings, and examples.

FIGS. 5A-5B show sagittal CBCT images of a deformable phantom (Playfoam™ beads in PlayDoh™ medium) before and after deformation and excision. The excision area (target volume) is highlighted dark shading (manually segmented), and the area immediately outside the excision (adjacent normal tissue) is highlighted in light shading (defined by automatic dilation of the target volume).

DETAILED DESCRIPTION

Figure 1:
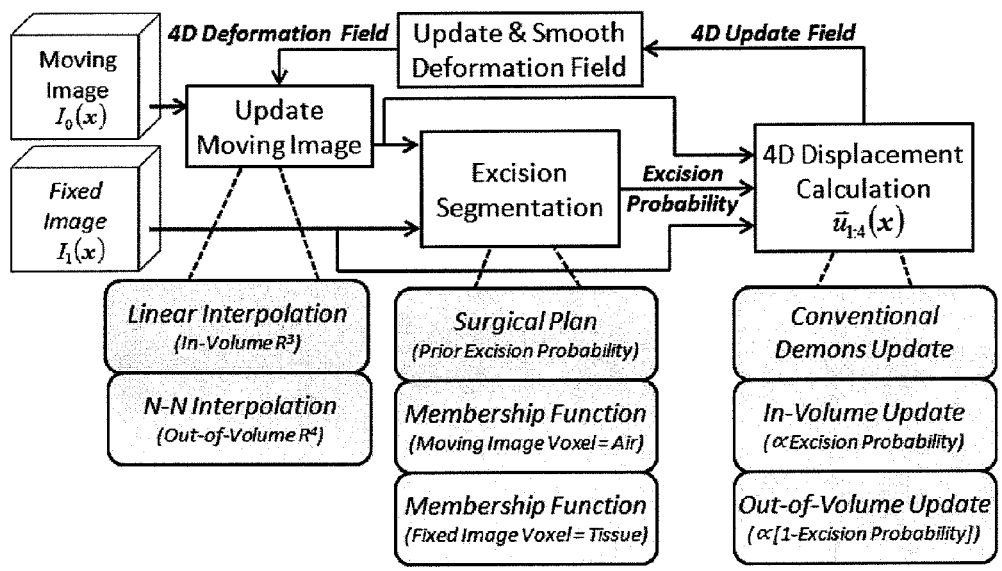
FIG. 1 is a schematic illustration of a system and method for registering images according to an embodiment of the current invention. It provides a flow chart illustrating a single iteration of the registration process (a variant of the Demons algorithm, referred to herein as the extra-dimensional Demons (XDD) algorithm) in which segmentation of the excised volume is integrated within the Demons registration framework.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Existing deformable registration methods generally fail to account for material excised or introduced between image acquisitions and typically simply "move" voxels within the images with no ability to account for tissue that is removed (or introduced) between scans. Materials of interest can include, for example, tissue (bone, muscle, fat, tumor, etc.) removed between scans or devices (e.g., needles, packing, staples, etc.) introduced between scans. However, the broad concepts of the current invention are not limited to these particular examples. We have developed an approach in which an extra dimension is added during the registration process to act as a sink for voxels removed between scans. An analogous method would include an extra dimension to serve as a source for voxels introduced between scans. A series of cadaveric images acquired using a prototype mobile C-arm for cone-beam CT (CBCT) was used to model tissue deformation and excision occurring during a surgical procedure according to an embodiment of the current invention, and the ability of deformable registration to correctly account for anatomical changes under these conditions was investigated. Using a previously developed deformable registration algorithm we identified the difficulties that traditional registration algorithms encounter when faced with excised tissue and have developed an algorithm better suited for use in intraoperative image-guided procedures in order that image registration can be performed while accurately accounting for tissue excision while avoiding erroneous deformations around the excision. The addition of extra dimension(s) to the registration problem (e.g., treating a 3D image as a 4D image, with the fourth dimension representing a sink for voxels "ejected" from the image) is shown to resolve spurious distortions suffered by conventional registration approaches.

According to an embodiment of the current invention, we hypothesized that a modified Demons algorithm that explicitly identifies and models tissue excision in the course of registration can provide superior registration performance compared to straightforward application of the conventional Demons approach in images featuring tissue excision. Specifically, an "extra-dimensional" Demons method (denoted XDD) is provided that adds a fourth dimension to the usual 3D registration problem into which voxels corresponding to tissues identified as missing in the fixed image may be ejected from the moving image. Although the focus of description below is on 3D medical images, the approach is general and may include 2D images (e.g., photographs, maps, etc.) and non-medical images.

As a starting point, we delineate a spectrum of scenarios involving missing tissue in surgical guidance: i.) tissue-in-air excision tasks [where tissues of interest include bone (e.g., osteotomy, ethmoidectomy, vidian canal drill-out, and clival drillout) and/or soft tissues (superficial fat/muscle resection, glossectomy, lung nodule resection, mucocele resection, and suction of fluid]); and ii.) soft tissue-in-tissue resection tasks (e.g., resection of a brain tumor, liver metastasis, etc. from within the surrounding medium of normal soft-tissue). In the first, the resected volume results in an air void, whereas in the second, surrounding soft tissue in-fills the resected volume. Initial development of the XDD concept detailed below according to an embodiment of the current invention focuses on the first scenario, in which tissue excision leaves an air volume in place of the missing tissue, although deformations of the surrounding normal tissue may have occurred. The tissue-in-air scenario corresponds to a broad spectrum of surgeries, including head and neck/skull base surgery.

Previous work has identified that for accurate deformable registration in the presence of excisions, the excision area must be identified and accounted for accurate registration,[17] and identification of "missing data" regions may be performed concurrently with the registration process.[18] For example, Risholm et al.[19,20] used a Demons variant for MR-guided brain surgery and recognized that erroneous deformations were calculated within areas of resection, and these errors were found to degrade the overall registration solution. They developed a novel variant of the Demons algorithm for registration of intraoperative MRI brain images in which excisions were identified by a level-set segmentation method, and the Gaussian smoothing step of the Demons algorithm was replaced with a filter designed to accommodate errors caused by retraction of brain tissue and resection of tumor.

Some embodiments of the current invention are distinct in methodology (the addition of an extra dimension in the registration problem), motivation (to reduce the effect of spurious distortions induced by missing tissue, while maintaining the speed and simplicity of the Demons algorithm), and application (CBCT-guided head and neck/skull base surgery). The conventional and XDD forms of the Demons algorithm are tested in phantom and simulation to illustrate and quantify the behavior of deformable registration in the presence of missing tissue in some examples below. Further experimental validation involved a series of cadavers undergoing ethmoidectomy, vidian canal drillout, and clival drillout corresponding to endoscopic skull base surgery. The performance of conventional Demons and XDD was quantified in terms of image-based metrics [e.g., normalized cross-correlation (NCC) and normalized mutual information (NMI) between deformed and fixed image volumes], target registration error (TRE), and the accuracy of voxels identified as either "missing" (and therefore ejected by XDD) or normal (and therefore preserved).

FIG. 1 is a schematic illustration of a system and method for registering images according to an embodiment of the current invention. The system can include an image registration unit that is configured to perform the image registration as illustrated in FIG. 1. The image registration unit can be a computer or portion of a computer, for example, and can be integrated into other equipment. For example, the image registration unit can be integrated into an image-guided intervention system, such as an image-guided radiation therapy (IGRT) or image-guided surgery (IGS) system. For example, it may be integrated into CT, CBCT or magnetic resonance systems. However, the systems and methods according to the current invention are not limited to these examples. Medical imaging applications are one area where embodiments of the current invention can be utilized. However, any system or method in which two or more images are being registered, whether they are two-dimensional or three-dimensional images, could be a potential application of embodiments of the current invention. For example, some embodiments of the current invention can be directed to, but are not limited to, photography, microscopy, satellite imagery, etc.

The image registration unit according to some embodiments of the current invention is configured to receive first image data $I_0(x)$ for a first image in an N-dimensional space, receive second image data $I_1(x)$ for a second image in the N-dimensional space, calculate a field of update vectors $\bar{u}(x)_{M:N+M}$ that maps the first image into a moving image, and map the first image into the moving image using the field of update vectors such that the moving image more closely matches the second image. In other words, the first image is modified using the update vectors such that the resultant modified image is a better match to the second image than the original first image was. FIG. 1 is an example of N=3 and M=1, but the general concepts of the current invention are not limited to this example. The field of update vectors $\bar{u}(x)_{M:N+M}$ include a plurality of N+M dimensional update vectors, each update vector having N spatial components and M extra components. N is an integer greater than zero and M is also an integer greater than zero. The M extra components of the plurality of update vectors identify portions of the first image that are assigned external values during the mapping the first image into the moving image.

The process of calculating update vectors and modifying the original or last modified image and mapping into another moving image can be repeated a plurality of times to iteratively improve matching of successive moving images to the second image. The plurality of times can be a predetermined number. In other words, the loop in FIG. 1 would terminate after the specified number of iterations have been performed. In another embodiment, the plurality of times can be determined based on a measure of change between successive iterations. Additional functions can be performed on the moving image such as filtering, e.g., smoothening, as is indicated in FIG. 1.

In some embodiments of the current invention, the portions of the first image that are assigned external values during the mapping into the moving image correspond to at least one of removal or addition of image portions to the first image relative to the second image. In some embodiments, the first image includes an image of an object and the second image includes an image of the object in which a section of the object is absent. In this embodiment, the portions of said first image that are assigned external values during the mapping into the moving image correspond to the section of the object that is absent in the second image. In some embodiments, the assigned external values during the mapping into the moving image correspond to an object introduced into the second image that was absent from the first image. For example, a surgical tool may be present in the second image but not in the first. This is just one illustrative example and not intended to limit the broad concepts of the current invention.

In some embodiments of the current invention, the M extra components of the update vectors are assigned values based on a probability that an external value is to be assigned during the mapping the first image into the moving image. In some embodiments, the probability can include a weighting factor to weight some of the plurality of update vectors more strongly for assigning the external value than other of the plurality of update vectors.

In some embodiments of the current invention, N=3 and M=1 as is illustrated in the example of FIG. 1. In some embodiments, the first image can include an image of tissue and the second image can include the image of the tissue that has a portion excised. In this case, the portions of the first image that are assigned external values during the mapping into the moving image are assigned background image values corresponding to absence of tissue to correspond to the portion excised. In some of the examples below, and in the example of FIG. 1, such introduced values are referred to as "air".

The following examples will help further describe some concepts of the current invention as well as describe some particular applications. However, the broad concepts of the current invention are not limited to these particular examples.

EXAMPLES

Registration Methods
  Conventional Demons Registration
  A previously reported variant of the symmetric-force Demons algorithm was employed as a reference and basis of comparison.[9,12,14] The method has been validated in phantom, cadaver, and clinical studies to provide geometric accuracy to within approximately the voxel size (~0.5 mm) for typical deformations encountered in CBCT-guided head and neck surgery. The Demons registration framework consists of a series of iterative steps. First, an update vector field is calculated based on currently overlapping voxel intensities. Second, the update field is added to the existing solution (initialized either by a zero field or by rigid registration), and the resulting deformation vector field is regularized by smoothing with a Gaussian kernel. Finally, the smoothed deformation field is used to update the moving image, and the process is repeated with the updated version of the moving image.

The update field, $\vec{u}$, is calculated based on the image intensities of the moving and fixed images, denoted $I_0$ and $I_1$ respectively, at each overlapping position in the images:

$$\vec{u}(x) = \frac{2[I_0(x) - I_1(x)][\vec{\nabla} I_0(x) + \vec{\nabla} I_1(x)]}{K[I_0(x) - I_1(x)]^2 + \left\|\vec{\nabla} I_0(x) + \vec{\nabla} I_1(x)\right\|^2} \quad (1)$$

where the normalization factor K is the reciprocal of the squared voxel size (units $1/mm^2$).[11] The update field is then added to the existing solution, and the result is convolved with a Gaussian kernel such that the deformation field, $\vec{D}$, at iteration n is given by:

$$\vec{D}_n = G_\sigma * (\vec{u}_{n-1} + \vec{u}_n), \quad (2)$$

where * indicates 3D convolution, and the width of the Gaussian kernel σ was fixed to 1 voxel for all experiments described below. The deformation field is then used to update the moving image, and the registration process is repeated iteratively.

We consider the "moving" image, $I_0$, as the image obtained at an earlier time-point that is to be registered to a more up-to-date image. Similarly, the "fixed" image, $I_1$, is the up-to-date image to which the moving image is to be matched. For example, the moving image could be a preoperative CT, and the fixed image an intraoperative CBCT obtained at the time of surgery, allowing registration of preoperative imaging and planning data to the intraoperative scene. Alternatively, the moving image could be a CBCT acquired at the beginning of a procedure (into which CT and planning data have been registered as in the previous sentence), and the fixed image a CBCT acquired at a later point in the procedure. In this manner, registration continually moves image and planning data "forward" to the most up-to-date geometric context that matches the state of the patient at any point in the procedure.

Registration is carried out according to a multi-resolution morphological pyramid to improve registration speed and robustness against local minima. The images are binned and downsampled by factors of 8, 4, 2, and 1 (denoted DS8, DS4, DS2, and DS1, respectively), and registration is performed first at the coarsest level, with the result at each level initializing registration in the subsequent level at finer detail. In the examples described below, the number of registration iterations was set at (15, 25, 25, and 15) for (DS8, DS4, DS2, and DS1, respectively) based on observation of the convergence rate. Previous work[15] demonstrated an optimized convergence criterion based on the difference between subsequent deformation fields (as opposed to a fixed number of iterations per level); however, the current examples fixed the number of iterations for all cases to maintain consistency across experiments and study the effect of the "extra-dimensional" component specifically. Previous work[16] also demonstrated a Demons variant with an iterative intensity matching process that overcomes errors associated with image intensity mismatch between the fixed and moving images; however, since all cases considered below involved CBCT-to-CBCT registration of images acquired on the same, calibrated CBCT imaging system, the iterative intensity match process was not needed.

Extra-Dimensional Demons (XDD) Registration

Extra Dimension

Figure 2:
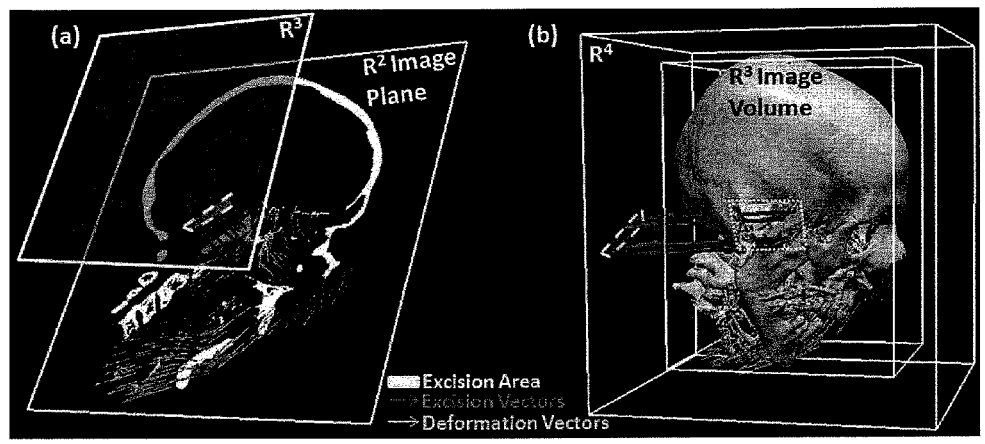
FIGS. 2A-2B provide a schematic illustration of XDD for (a) 2D and (b) 3D image registration according to some embodiments of the current invention. Deformations are represented by in-plane/in-volume vectors (dark shading), and voxels identified within a region of excision (light shading) are subject to out-of-plane/out-of-volume "deformation" (i.e., excision).

A novel concept in XDD is to account for tissue excision by an increase in the dimensionality of the solution from three dimensions to include a fourth dimension into which voxels may be moved if identified as belonging to an excision (or conversely from which air may enter the image in the region of the excision). In conventional Demons registration, the update and deformation fields consist of vectors of the same dimensionality as the image space. Therefore, registration of two 3D image volumes involves a 3D deformation field made up of 3D vectors. We denote the 3D volume domain as $R^3$ with coordinates (x,y,z) or equivalently $(x_1,x_2,x_3)$. Conventional deformable registration therefore operates entirely within $R^3$. The framework is extended according to an embodiment of the current invention so that the solution for a 3D registration is a 3D deformation field made up of 4D vectors. As illustrated in FIG. 2, this effectively adds a fourth dimension (for 3D image registration) into which voxels may be "ejected" (or equivalently, from which voxels with image intensity corresponding to air enter the volume). As detailed below, motion along the fourth component is only considered if a voxel satisfies specific criteria identifying it as part of an excision. Within the XDD framework, therefore, the vectors comprising the fields given by Eqs. (1) and (2) are 4-vectors, with the first three components representing deformation in $(x_1,x_2,x_3)$, and the fourth component representing excision. FIG. 2 illustrates the method in (a) a 2D image registration (more easily visualized within the constraints of 2D display) wherein excised regions are ejected from $R^2(x_1,x_2)$ to a $R^3$ hyperplane, and (b) a 3D image registration in which excised regions are ejected from R3 $(x_1,x_2,x_3)$ to a $R^4$ hypercube.

The main challenge in such an approach is assigning the value of the fourth component of the deformation field so that only those voxels truly representative of excised tissue are removed during the registration process. Since the gradient between $R^3$ and $R^4$ is intrinsically steep, the entire 3D image would tend to move to $R^4$ without constraint if the standard Demons force was applied in all dimensions. We therefore first identify the region likely to be associated with excision automatically by segmentation performed simultaneous to the iterative registration process. By performing segmentation simultaneously with the iterative registration process (as opposed to using a single initial segmentation), the process allows progressively more refined estimates of the excision volume as other tissue is deformed and improves robustness to segmentation error. This allows a fairly simple segmentation method detailed below—intensity thresholding of tissue to be ejected versus air (i.e., the material remaining in the voxel for the tissue-in-air "drill-out" scenario). It also allows the possibility of recovery from segmentation error by bringing voxels back to $R^3$ if erroneously ejected in previous iterations.

The method according to this embodiment is illustrated in FIG. 1, showing the segmentation and 4D force calculation modifications to the conventional Demons framework. At each registration iteration shown in FIG. 1, the estimate of voxels to be excised is based on the currently registered set of images. Segmentation of voxels possibly to be "ejected" employs a probability (membership function) computed from the image intensities. In subsequent registration steps, the magnitude of the "out-of-volume" component of the update force vector field is calculated proportional to the excision probability. The segmentation and extra-dimensional force calculation are detailed in the following sections.

Identifying Excised Voxels

Initial implementation of XDD used a fairly simple segmentation method to identify candidate voxels for "ejection" based on an air-tissue intensity threshold appropriate to the tissue-in-air excision scenario (e.g., bone drill-out task). Given an intensity threshold T, two probabilistic membership functions (i.e., the probability that a voxel is associated with tissue or air) are computed at every location in the images as follows:

$$P_{moving}^{tissue}(x)=\text{sigm}(I_0(x),\alpha,T) \qquad (3)$$

$$P_{fixed}^{air}(x)=\text{sigm}(I_1(x),-\alpha,T) \qquad (4)$$

where the sigmoid function is:

$$\text{sigm}(I,\alpha,T) = \frac{1}{1+e^{-\alpha(I-T)}} \qquad (5)$$

The membership function $P_{moving}^{tissue}$ is the probability that a particular voxel in the moving image corresponds to tissue (not air), and $P_{fixed}^{air}$ is the probability that a particular voxel in the fixed image corresponds to air (not tissue). The parameter α controls the "steepness" of the sigmoid, and the probability $P_{excision}$ of a given voxel belonging to excised tissue is given by the joint probability of Eqs. (3) and (4):

$$P_{excision}(x)=P_{moving}^{tissue}(x) \cdot P_{fixed}^{air}(x) \qquad (6)$$

Simply interpreted, Eq. (6) states that if a given voxel in the moving image is likely tissue, and that same voxel in the fixed image is likely air, then that voxel likely corresponds to "missing tissue" (i.e., tissue removed from the volume between the moving and fixed images), and thus it is assigned a higher probability of being excised. This interpretation is strictly valid only if images are perfectly registered and would not be expected to hold if images are misaligned—thus the motivation for incorporating the segmentation within the iterative registration process as shown in FIG. 1 to allow improved segmentation in each iteration. FIG. 3 shows example tissue and air membership functions along with the resulting excision probability "map" (i.e., $P_{excision}$ computed as a function of the fixed and moving image intensity). The example calculation corresponds to the deformable phantom used in studies detailed below, with T=0.003 mm$^{-1}$ and α=1000.

However, note that the sigmoid functions are just one example of a way of segmenting tissue. Other functions, including a simple scalar threshold value for example, and other, more sophisticated methods of image segmentation can be used in other embodiments. For example, segmentation can be based not only on the image value but also on parameters of shape, connectedness, etc. Segmentation is a very large and sophisticated field, and the sigmoids are just one example.

Incorporation of a Surgical Plan

The product of probabilities in Eq. (6) treats all areas of the image as equally likely to experience an excision; however, this is an oversimplification as there is almost always a volume of interest (i.e., the region of surgical approach and the volume about the surgical target) which is known a priori to be more likely to be excised. Direct implementation of Eq. (6) was found to be somewhat prone to false positives (i.e., voxels falsely identified as "excised" and ejected from the volume) arising from image noise, artifact, or gross misregistration. To mitigate such effects, and to use available prior knowledge where available, a probabilistic mask ($P_{plan}$, referred to as the surgical "plan") was included in the joint probability. The mask acts as a weighting function that increases the probability of excision about the site of anticipated approach and excision and decreases it at locations distant from the excision:

$$P_{excision}(x) = P_{moving}^{tissue}(x) \cdot P_{fixed}^{air}(x) \cdot P_{plan}(x) \quad (7)$$

The mask function was defined simply as a long-range Gaussian cloud with peak value 1.0 centered roughly on the expected excision site and falling off with distance according to a free parameter ($\sigma_{plan}$) corresponding to the estimated size of the excision, thus constraining excisions to a region local to the expected surgical site. As shown in FIGS. 4A-4D for the cadaver experiments described below, the Gaussian mask can be coarsely tuned depending on the extent of anticipated excision. For example, as in FIG. 4A, the surgical plan can be placed narrowly ($\sigma_{plan}$=10 mm in all directions) about the vidian canal (a structure drilled out and followed on approach to the skull base) and the clivus (the bone volume at the skull base that would be drilled out if infiltrated with tumor). Alternatively, as in FIGS. 4C-4D, the surgical plan can be placed broadly ($\sigma_{plan}$=15 mm in (LR,SI) directions and 30 mm in the AP direction) to encompass the ethmoid sinuses. In practice, the $P_{plan}$ multiplier in $P_{excision}$ was found to reduce erroneous "salt-and-pepper" excisions far from the actual excision—particularly in areas of image noise and artifact.

Extra-Dimensional Deformation Calculation

Tissue excision is modelled in the registration process by way of an additional (fourth) component of the deformation field vectors, denoted $\bar{D}_4$, whereas normal deformations (i.e., movement within $R^3$) are described by the in-volume components $\bar{D}_{1:3}$. When calculating the update field, the conventional Demons algorithm force is computed for the in-volume components as in Eq. (1), with the resulting three-vector reduced in proportion to $(1-P_{excision})$:

$$\bar{u}(x)_{1:3} = (1-P_{excision}(x)) \cdot \bar{u}(x) \quad (8)$$

In this way, regions far from the excision site (i.e., where $P_{excision} \rightarrow 0$) experience deformations approximating those in the conventional Demons approach.

The extra-dimensional ("out-of-volume") component of the update field, $\bar{u}_4$, is computed based on the joint probabilities $P_{moving}^{tissue}$, $P_{fixed}^{air}$, and $P_{plan}$ calculated in the previous segmentation step as:

$$\bar{u}(x)_4 = P_{excision}(x) \cdot k_{force} \cdot a_{vox} \quad (9)$$

such that the fourth component of the update field is a function of the excision probability for each voxel. A (optional) proportionality constant $k_{force}$ allowed the magnitude of the out-of-volume vector component to be increased or decreased to eject voxels farther or nearer into the $R^4$ hypercube at each iteration. The parameter was fixed to a value of $k_{force}$=1.0 (dimensionless) in all experiments reported below. The term $a_{vox}$ is the voxel size at the current level of the morphological pyramid. Addition of the 4D update field to the current estimate of the 4D deformation field, followed by 4D Gaussian smoothing, was performed as in conventional Demons registration and with the same smoothing parameters (but with increased dimensionality).

Image Update

Through the process described above, voxels that are identified as excised see the value of the fourth component of the deformation field increase with each iteration. As shown in FIG. 1, it is during the image update step that excisions (if any) are introduced into the moving image. As in conventional Demons registration, in-volume deformations are handled by linear interpolation of surrounding intensity values. Deformations represented by the fourth component of the deformation field (i.e., out-of-volume motion) can analogously be considered as a nearest-neighbor interpolation in which the extra-dimensional space is treated as an air-filled void for the tissue-in-air excision scenario considered here. Therefore, voxels for which the fourth component of the deformation field is large enough (i.e., far enough into the $R^4$ hypercube) are assigned an air intensity value upon update of the moving image. The displacement beyond which excision is considered to have occurred constitutes a "horizon" in the fourth dimension, the threshold for which is written as $a_{vox} \cdot k_{horizon}$. The paramater $k_{horizon}$ may be freely adjusted to modify the "gravity" of the $R^3$ space—i.e., the ease with which voxels may escape the volume. Following a sensitivity analysis demonstrating relative invariance of the resulting deformation across a range in $k_{horizon}$ (0.5-1.5), a value of $k_{horizon}$=1.0 was chosen for all experiments reported below. The implication: a voxel exhibiting a displacement with $\bar{D}_4 > a_{vox}$ is subject to ejection on the current iteration.

Multi-Resolution Implementation

As with conventional Demons, XDD was implemented in a multi-resolution morphological pyramid with the same downsampling factors as described above (DS8, DS4, DS2, and DS1). For multi-scale XDD, the magnitude of the fourth component of the deformation field, $\bar{D}_4$, was "reset" to zero between levels of the morphological pyramid to reduce spurious ejection in the first iteration of the new level. A variety of multi-resolution XDD scenarios was examined in which the extra-dimensional aspect of the registration was turned on or off at various levels of the hierarchical pyramid—e.g., using conventional Demons at the DS8 level to provide coarse alignment and turning "on" XDD at the finer scales in DS4, DS2, and DS1.

Experimental Methods

Experiments were carried out to characterize the behavior of both the conventional Demons and the XDD embodiment of the current invention in the presence of excised tissue in the fixed image. Three main experiments were performed. First, a custom deformable phantom was imaged in CBCT, before and after deformation and with a volume of material excised between the "preoperative" (moving) image and the "intraoperative" (fixed) image. Test cases involved deformation-only, excision-only, and deformation+excision. Second, simulation studies were conducted using images of the same phantom in which simulated excisions of varying size were imparted. Such phantom experiments allowed variation and sensitivity analysis of the parameters intrinsic to XDD. Finally, cadaver experiments were performed to quantify and validate XDD registration performance in data featuring realistic anatomy and surgical excisions in the context of CBCT-guided endoscopic skull base surgery.

Phantom and Simulation Studies

As illustrated in FIGS. 5A-5B, a simple deformable (and excisable) phantom was constructed from a mixture of two materials—PlayFoam™ (Educational Insights, Lake Forest Ill.) sculpting beads embedded in a medium of PlayDoh™ (Hasbro, Pawtucket R.I.)—to form a roughly cylindrical shape ~6 cm in diameter, ~10 cm in height. This simple model provided high contrast between internal features and the background medium (~400 HU) which could be both deformed and excised. The visibility of individual PlayFoam™ beads (each ~1-2 mm diameter) allowed visual assessment of deformations and spurious distortion that would not be evident in a uniform phantom. As a further aid to quantifying registration accuracy, a collection of 3.2 mm diameter acrylic spheres were mixed within the phantom to provide uniquely identifiable "target" points in analysis of TRE.

The phantom was manually deformed (without excision) to emulate a deformation-only case, with CBCT images acquired before ($I_0$) and after ($I_{def}$) the deformation. Subsequently, as shown in FIG. 5B, an irregular volume (~1 cm³) was excised from the midsection of the phantom using a curette and tweezers (without further deforming the phantom), and a third CBCT image ($I_{def+exc}$) was acquired after the excision. The resulting three CBCT image pairs ($I_0$-$I_{def}$, $I_{def}$-$I_{def+exc}$, and $I_0$-$I_{def+exc}$) therefore emulate cases of deformation-only, excision-only, and deformation+excision. Registration was performed with both the conventional Demons and XDD methods in each case. Registration accuracy was quantified globally (i.e., across the entire image) and locally (i.e., within the immediate area of the excision) as described below.

The CBCT images acquired in the phantom study were then extended to a simulation study to investigate the effect of excision size on registration accuracy and the robustness of XDD registration in the presence of larger excisions. The simulated data were formed from the $I_{def+exc}$ image in which the excision volume was manually delineated (shown in dark shading in FIGS. 5A-5B). Simulated images were formed in which the excision volume was increased in size by dilating the excision volume with kernels of increasing size, thus expanding the excision to arbitrary size by digitally "blanking" the dilated region to the image intensity of air (0 mm⁻¹). Simulated excision volumes ranging in size from 2.5 cm³ to 17 cm³ were investigated. Deformable registration was performed to match the $I_0$ image to each of the simulated $I_{def+exc}$ images, and registration accuracy was evaluated as described below.

Figures 3A, 3B:
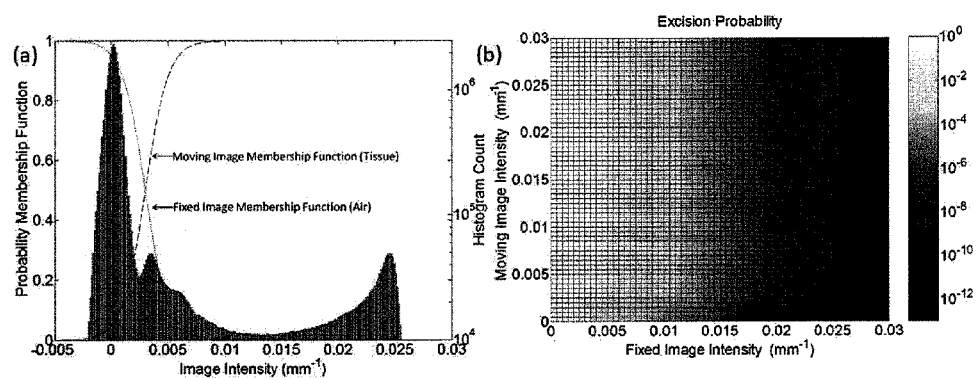
FIGS. 3A-3B provide (a) Illustration of tissue and air membership functions used in segmenting regions of excision. The histogram corresponds to a CBCT image of the phantom in FIGS. 5A-5B. (b) The resultant probability map [i.e., joint probability given by the product of membership functions in (a)] as a function of the fixed and moving image intensities.
Figures 4A, 4B, 4C, 4D:
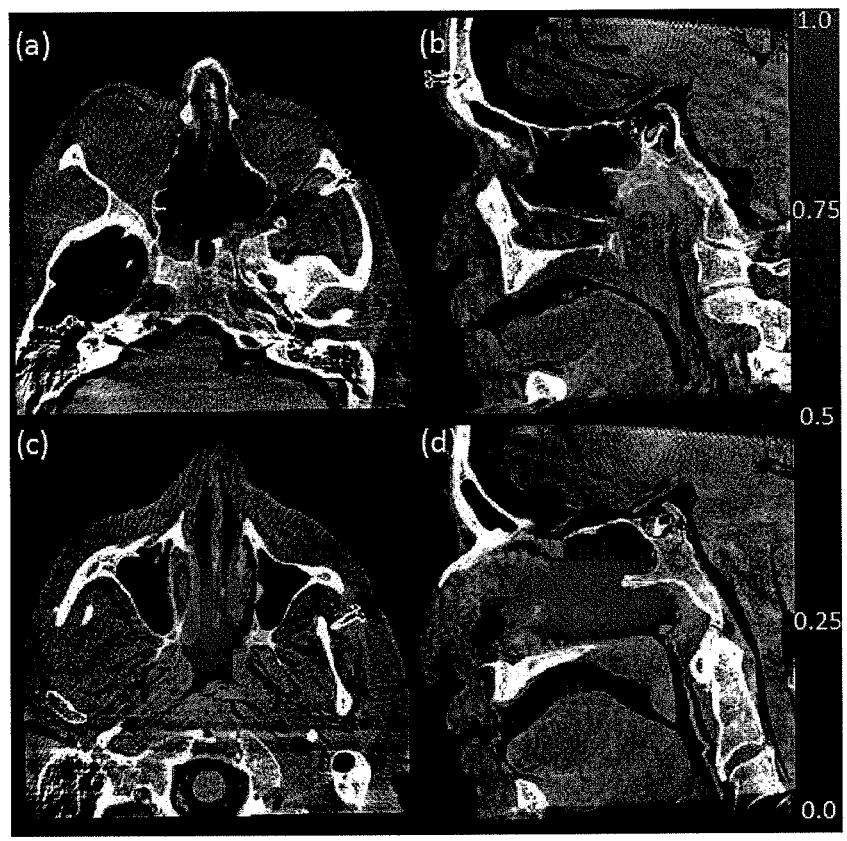
FIGS. 4A-4D provide illustrations of two example probability maps ($P_{plan}$) associated with anticipated regions of tissue excision. (a,b) Example of plan (shading) for drillout of the vidian canal overlaid on axial and sagittal views of a CBCT image. (c,d) Example large plan overlay.

For both the real phantom and simulation studies, the segmentation parameters shown in FIGS. 3A-3B were held fixed, giving a threshold near the air boundary and with relatively sharp transition from air to tissue. Other parameters (e.g., $k_{force}$ and $k_{horizon}$) were varied in sensitivity analysis, but none showed dramatic variation in the resulting deformation over the range investigated and the nominal values mentioned above were held fixed.

Registration accuracy was evaluated qualitatively and quantitatively. Visually, the quality of registration was assessed by examining the extent of distortion in the registered image—e.g., apparent shearing of the circular Play-Foam™ beads. Quantitatively, the registration accuracy was assessed in terms of the TRE measured as the distance between the centroids of the implanted acrylic spheres in the fixed and moving images before and after registration. In addition, the registration accuracy was assessed in terms of image-based metrics, NCC and NMI, computed across the entire image (global assessment) and in a smaller region about the excision. As shown in FIGS. 5A-5B, NMI was measured in the combined regions of excision (dark, central shading) and adjacent "normal" tissue (surrounding, lighter shading). The area immediately about the excision arguably requires the most accurate registration (e.g., to assess proximity of the drill-out to nearby critical anatomy, such as the carotid arteries in a clival drill-out), and it was hypothesized that this region would be most susceptible to spurious distortion in the conventional Demons approach.

Cadaver Study

Finally, cadaver experiments were performed using three fixed human head specimens undergoing endoscopic skull base surgery guided by C-arm CBCT.[21-23] A fellowship-trained neurosurgeon and ENT surgeon performed drill-out tasks pertinent to trans-sphenoid skull base surgery in each head, and CBCT images were acquired before and after intervention. Three drill-out tasks were evaluated (in reverse order): i.) drill-out of the clivus, the bone volume posterior to the sphenoid sinus bounded laterally by the carotid canals and posteriorly by the brain; ii.) drill-out of the vidian nerve canal, the bilateral corridor that provides an important landmark on approach to the clivus; and iii.) excision of the anterior and posterior ethmoid air cells, the bony architecture bilateral to the nasal septum attaching the sinus turbinates and lamina papyracea.

For each cadaver excision task, registration was performed from the pre-excision to post-excision CBCT image. For XDD registration, a surgical plan (mask function) as shown in FIGS. 4A-4D was used to mitigate erroneous excision at large distances from the anticipated site of intervention. The segmentation threshold (T) was selected automatically based on the Otsu method[24]—specifically, T equal to half the Otsu threshold, generally giving a value near the edge of the air threshold. Setting the sigmoid parameter to $\alpha=0.01$ maintained approximately the same "steepness" of the threshold functions as in phantom experiments while accounting for the different intensity range in CBCT images reconstructed on an arbitrary 0-4000 scale (as opposed to an attenuation coefficient scale used in the phantom study).

Analysis of registration performance was carried out in a manner similar to that described above for the phantom experiments. The true excision area was manually segmented in the postoperative CBCT image. The area immediately surrounding each excision was defined as the adjacent normal tissue volume in which measures of registration quality were assessed. In addition to the image-based metrics of NCC and NMI computed across the entire image and within local sub-regions, the accuracy of XDD in correctly ejecting voxels within the excision volume (while preserving voxels in surrounding, un-excised normal tissue) was measured in terms of the excision "sensitivity" (i.e., fraction of excision volume correctly ejected, analogous to true-positive fraction) and "specificity" [i.e., fraction of surrounding normal tissue properly preserved, analogous to (one minus) false-positive fraction].

Results

Phantom and Simulation Studies

Basic Comparison of XDD and Conventional Demons.

Figures 6A, 6B, 6C, 6D:
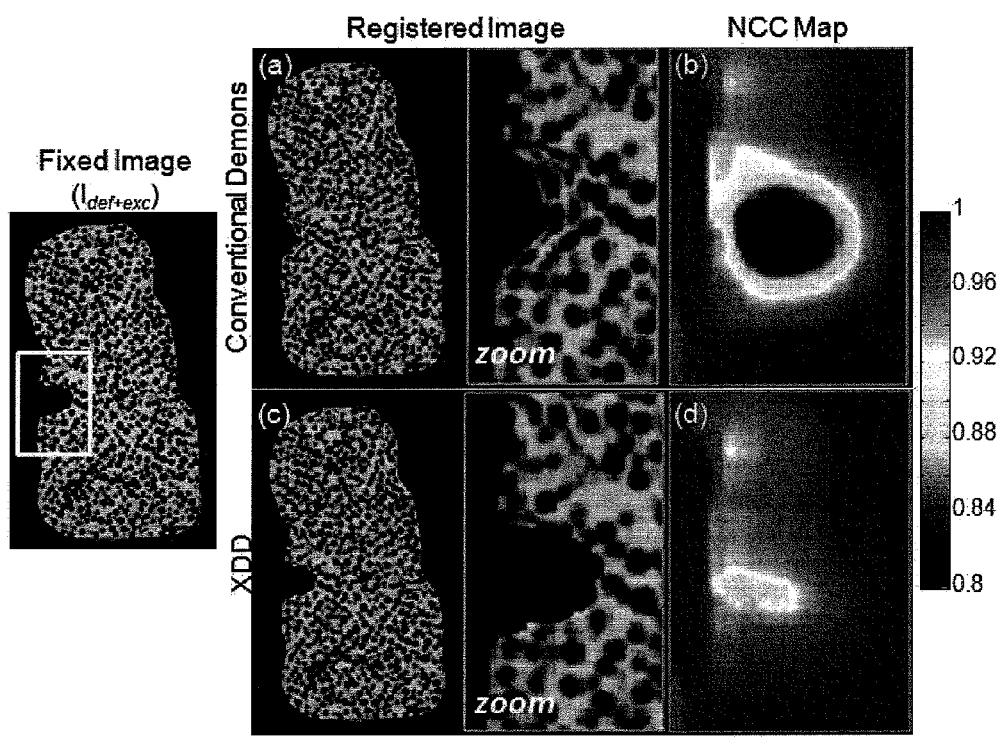
FIGS. 6A-6D provide Comparison of conventional Demons and XDD registration in a deformable phantom containing real deformations and a ~1 cm³ excision of material emulating a tissue-in-air excision scenario. Coronal slices from the CBCT volume are shown. (a) Registered image (and zoomed-in region) resulting from the conventional Demons approach, with (b) NCC map (across the zoomed-in region) computed using a 10×10×10 voxel sliding window across the region of interest. (c,d) The same, for the XDD registration approach. Whereas (a-b) exhibit unrealistic distortion and reduction in NCC, (c-d) demonstrates a fairly accurate ejection of voxels within the region of excision and maintenance of NCC (with reduction within the air void likely due to quantum noise).

FIGS. 6A-6D demonstrate image distortion imparted by the conventional Demons algorithm in the presence of missing tissue, evident as unrealistic warping of features within and adjacent to the region of excision. Registration accuracy at large distances (>~1 cm) from the boundary of the excision is largely unaffected and exhibits the expected (sub-voxel) precision demonstrated in previous work. The NCC map in FIG. 6B quantifies the failure in registration within and around the region of excision, where the conventional Demons approach appears to force tissue "inward" toward the boundary of the excision, but does not do so in a way that provides an accurate match to the fixed image. The performance of the XDD approach is shown in FIGS. 6C-6D, showing XDD registration results to be largely free of spurious distortion. The identification of excised tissue and modeled ejection of voxels within the iterative registration process provides a close match to the fixed image right up to the excision boundary and in the adjacent "normal" tissue, while maintaining the geometric registration accuracy of the conventional Demons approach in other regions of the image. The NCC map quantifies a higher degree of agreement between the deformed and fixed image, with a decrease in NCC in the central void of the excision likely due to a mismatch to quantum noise in air.

The locality of the excision effect involved in XDD and the maintenance of registration accuracy throughout the rest of the image is evident in the images of FIGS. 6A-6D, the NMI, and the TRE computed from the entire registered image. Specifically, the NMI computed over the entire image volume was identical (NMI=1.17) for conventional Demons and XDD registration, compared to NMI=1.09 for rigid registration (initialization). Conversely, in the area containing and immediately surrounding the excision, the results indicate degraded registration performance for conventional Demons registration (NMI=1.10) compared to the same region in XDD (NMI=1.16). Similarly, the TRE calculated from 6 acrylic "target" spheres embedded throughout the bulk of the phantom was (0.40±0.15) mm for conventional Demons and (0.40±0.15) mm for XDD, compared to (1.00±0.70) mm for rigid registration. These results verify that XDD maintains a high level of registration accuracy as demonstrated by the conventional Demons approach throughout the image volume (without excision), while improving performance and reducing or eliminating distortion in the region local to the excision.

Figure 7:
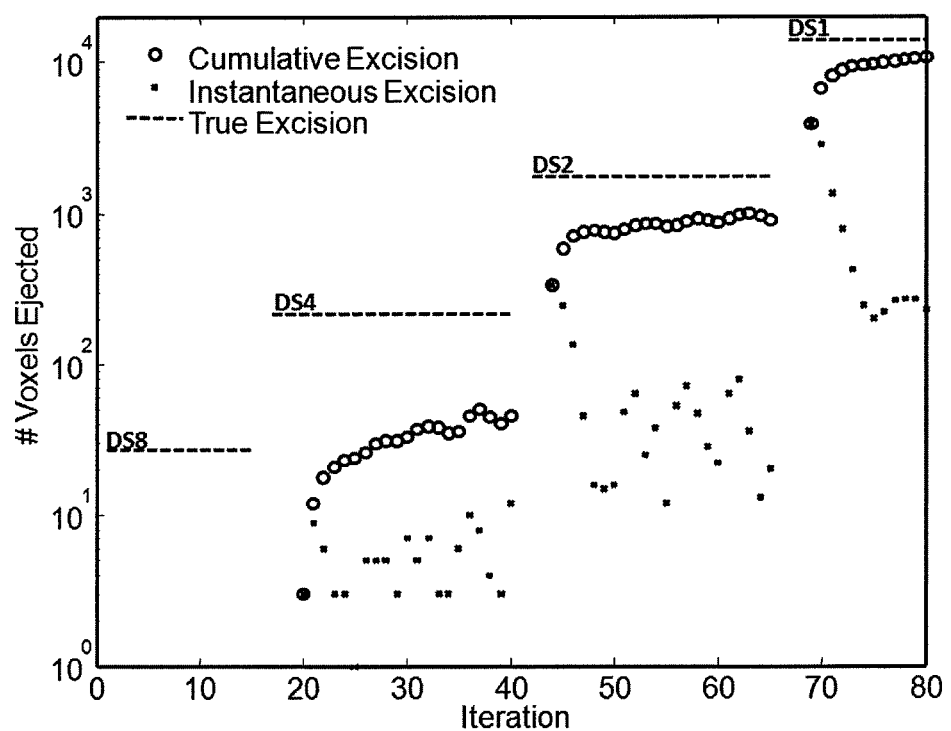
FIG. 7 shows evolution in the number of voxels excised from the 3D volume in XDD registration. Four levels of the morphological pyramid are evident (DS8, DS4, DS2, and DS1). The horizontal dashed line in each level marks the true number of voxels within the excision volume in the fixed image. The open circles mark the cumulative number of voxels ejected from the volume, whereas the small dots mark the (instantaneous) number of voxels ejected in a given iteration. For the nominal XDD parameters described in the text, a gradual, conservative convergence on the true excision volume is observed (without overshoot).

The evolution of the conventional Demons registration process across multiple levels of the morphological pyramid and iterations has been previously reported,[15] typified by a fairly monotonic increase in NCC (or other metric) with each iteration (with some variability in the first few iterations of each new level of the pyramid). The evolution of XDD was anticipated to be similar in terms of image metrics, but the approach introduces an additional question regarding the behavior of the excision effect—i.e., at which level of the pyramid (and at which iterations) are voxels "ejected" from the volume. As shown in FIG. 7, simultaneous 3D deformable registration and 4D "excision" exhibits a fairly monotonic evolution at each level of the pyramid. The cumulative excision gradually approaches the "true" excision volume at each level and converges fairly conservatively (i.e., does not overshoot) for the parameters employed. Within a given level of the pyramid, the largest number of voxels is ejected in the first few iterations, followed by a sharp decrease and nearly constant rate of ejection. The scenario illustrated is the nominal case in which XDD was "on" for all levels of the registration pyramid. Variations on this nominal scheme were tested, viz., "off" in the first (DS8) level, and "on" in the three subsequent levels (DS4, DS2, and DS1); however, it was generally found that using XDD at all levels of the morphological pyramid improved registration accuracy and reduced erroneous deformations that were difficult to correct in subsequent levels.

Registration Performance as a Function of Excision Size

Figure 8:
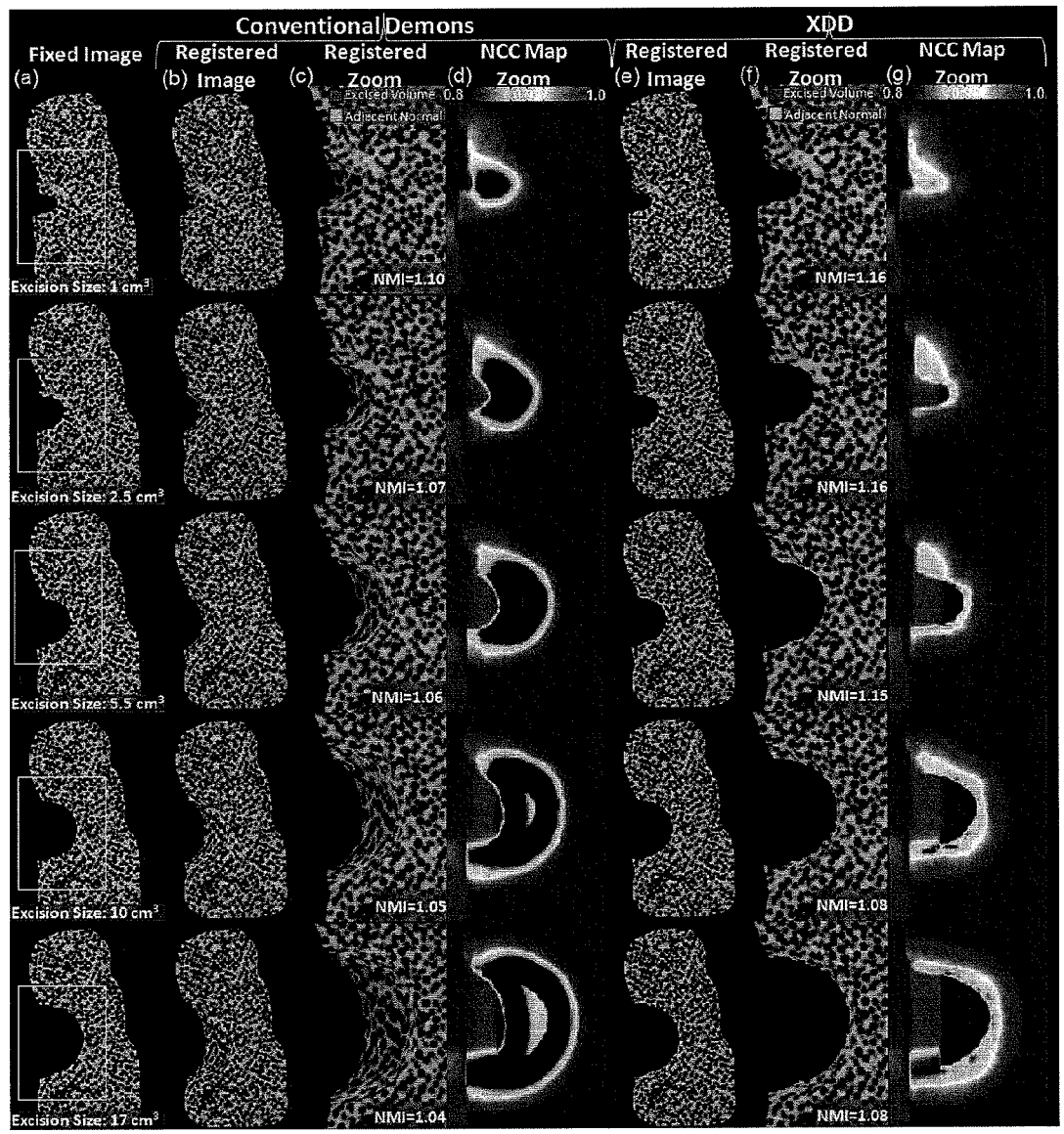
FIG. 8 shows dependence of deformable registration on the size of excision. A single coronal plane from the 3D volume is shown in each case. (a) Fixed images featuring an excision varying in size from ~1 cm³ (the real excision in FIGS. 5-7) to 2.5-17 cm³ (simulated excisions). Registered images and NCC map for the conventional Demons approach are shown in (b,c,d), and those for the XDD approach are shown in (e, f, g).
Figure 9:
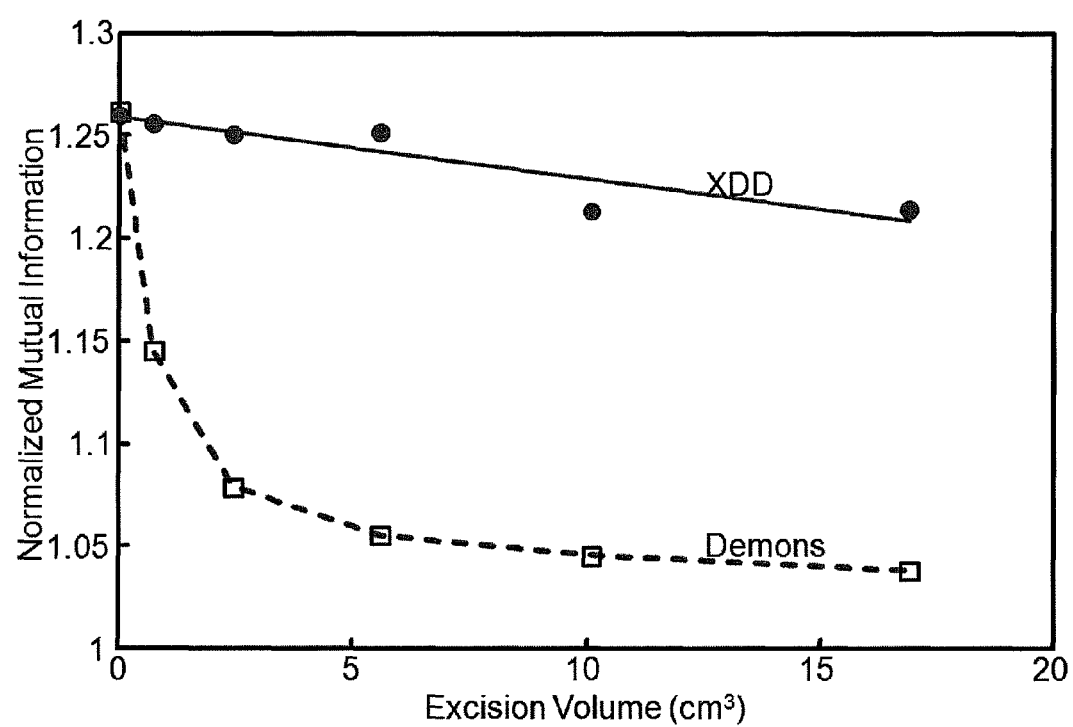
FIG. 9 shows dependence of deformable registration on the size of excision. While the performance of the conventional Demons algorithm declines sharply with excision size, NMI is maintained to a fairly high degree for the XDD approach. The first point on each curve (excision volume equal to 0 cm³) corresponds to the deformation-only case.

FIG. 8 shows the dependence of registration accuracy on the size of the excised volume for both the conventional Demons and XDD approaches. The ~1 cm$^3$ excision is the same as the real data considered in the previous section, and the larger excisions were simulated by dilation as described above. Some degradation in registration quality is evident for the larger excision volumes—visible as image distortion and quantified by the reduction in NMI for each case. The conventional Demons method suffers major distortion and gross misrepresentation of tissue within and around the excision, similar to that in FIG. 6 but amplified steeply for larger excisions. XDD registration on the other hand exhibited a high degree of robustness to excision across the full range of sizes investigated, with only a slight degradation of registration accuracy for the largest excisions. The results are quantified in FIG. 9, where NMI for the conventional Demons approach declines sharply with excision size, but XDD is fairly robust.

Cadaver Study

Figure 10:
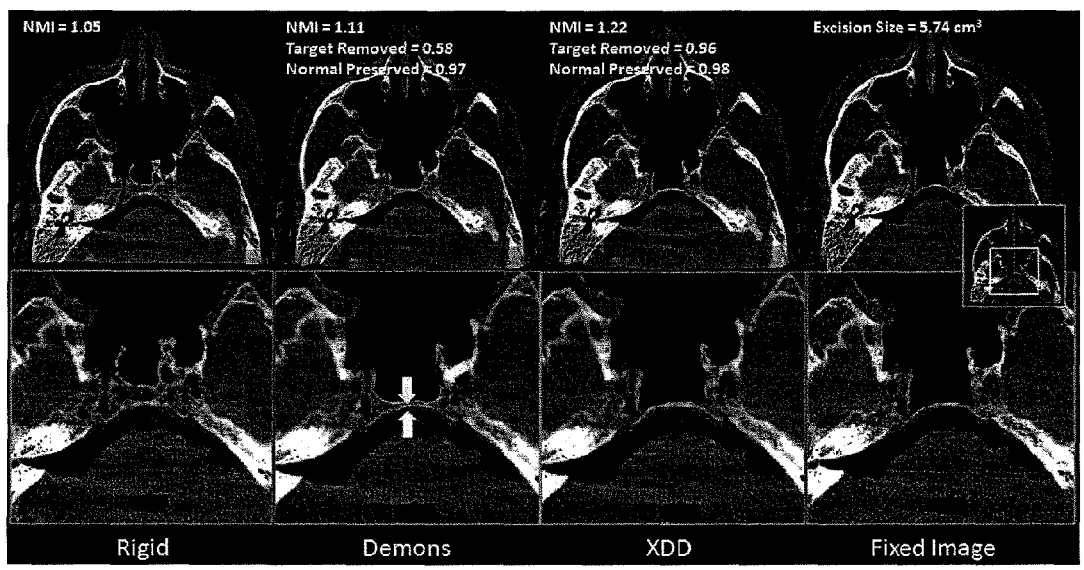
FIG. 10 shows deformable registration in the presence of tissue excision about the clivus. (a) Rigid registration of the preoperative image to the fixed image image shown in (d). (b) Conventional Demons registration exhibits spurious distortion and failure to account for missing tissue. Arrows highlight features of note in the text. (c) XDD registration, demonstrating a close match to the fixed image shown in (d).
Figure 11:
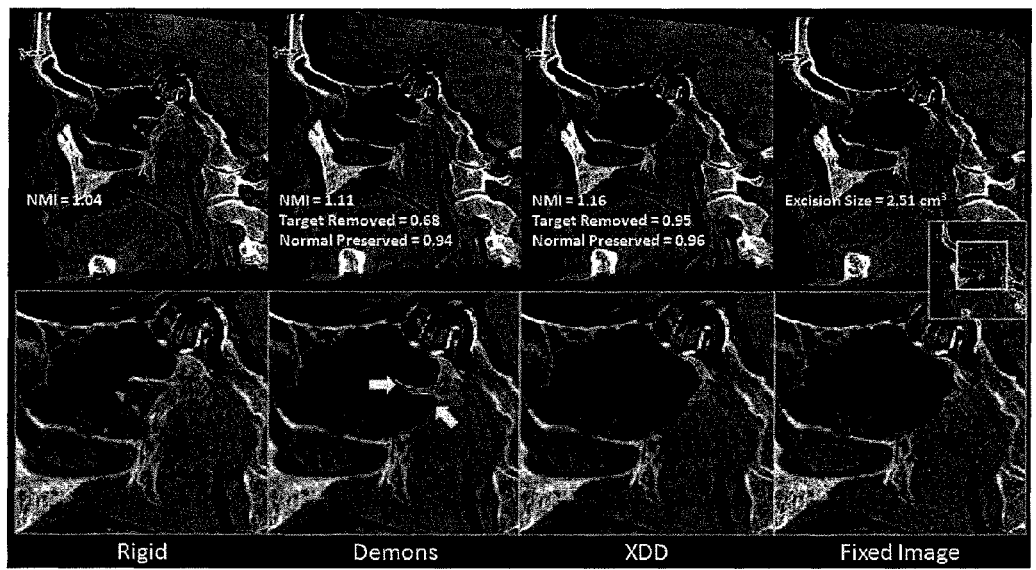
FIG. 11 shows deformable registration in the presence of tissue excision along the vidian nerve canal. (a) Rigid registration of the preoperative image to the fixed image shown in (d). (b) Conventional Demons registration exhibits spurious distortion and failure to account for missing tissue. Arrows highlight features of note in the text. (c) XDD registration, demonstrating a close match to the fixed image shown in (d).
Figure 12:
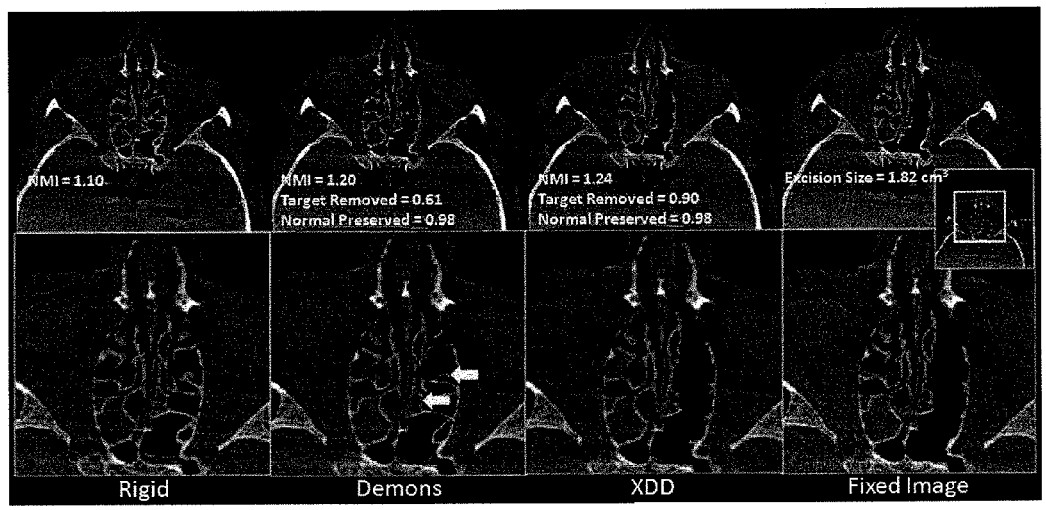
FIG. 12 shows deformable registration in the presence of tissue excision throughout the left ethmoid sinus. (a) Rigid registration of the preoperative image to the fixed image image shown in (d). (b) Conventional Demons registration exhibits spurious distortion and failure to account for missing tissue. Arrows highlight features of note in the text. (c) XDD registration, demonstrating a close match to the fixed image shown in (d).

The results for realistic skull base surgery drill-out tasks conducted in cadaveric specimens are summarized in FIG. 10 (clivus), FIG. 11 (vidian canal), and FIG. 12 (ethmoid sinuses). Overall, the results confirm the findings of the phantom and simulation studies: the conventional Demons approach suffers distortions in the presence of excisions and a quantifiable reduction in NMI and other metrics. The XDD approach accounts for missing tissue and maintains overall geometric accuracy in the deformable registration. A few notable features are highlighted by arrows in FIGS. 10-12. For the clival drill-out (FIG. 10), conventional Demons causes the anterior clival wall to collapse onto the posterior wall, and bony structure lateral to the excision site to collapse unrealistically. XDD yields an image closely matching the fixed image in terms of both the excision site and adjacent anatomy. For the vidian canal drill-out (FIG. 11), conventional Demons collapses and distorts the bony architecture of the middle cranial fossa and pterygopalatine plate to yield a false bony protrusion within the sinus space. XDD properly reproduces the excision and exhibits little or no distortion of surrounding architecture. For the ethmoid air cell excision (FIG. 12), conventional Demons induces spurious deformations and thinning of air cell walls and even introducing an apparent (false) air cell in the excision site. Errors in the deformable registration are evident in soft tissues medial to the excision site. Again, XDD performs comparably well, even partially accounting for differences in fluid filling of the sinuses between the preoperative and intraoperative images.

Figure 13A:
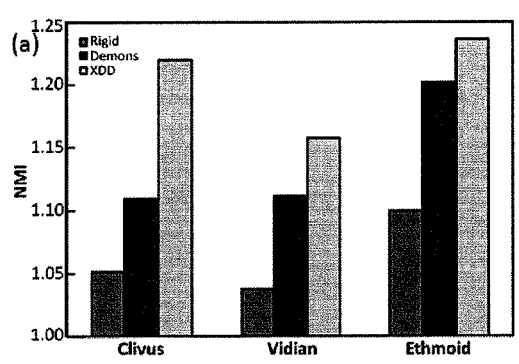
FIG. 13 shows registration performance in cadaver studies emulating CBCT-guided skull base surgery involving drillout tasks of the clivus, vidian canal, and ethmoid sinuses. (a) NMI for rigid, conventional Demons, and XDD registration. (b) Accuracy in and about the region of excision in the form of "operating curves"—i.e., fraction of target tissue correctly removed ("sensitivity") plotted versus fraction of adjacent normal correctly preserved ("specificity").
Figure 13B:
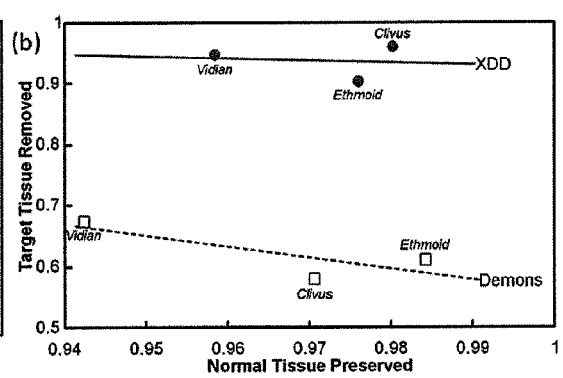

These qualitative observations are confirmed in the quantitative figures of merit shown in FIG. 13. The NMI demonstrates an increase in registration accuracy for the XDD approach in each case, and the metrics of excision sensitivity and specificity show that the excision areas are correctly modeled to a level of 90% or greater. XDD demonstrates improvement in sensitivity (i.e., fraction of target volume accurately removed) in each case (from ~60% for conventional Demons to >90% for XDD). We had hypothesized a possible reduction in "specificity" (i.e., fraction of adjacent normal tissue correctly preserved) for XDD due to false-positive ejection of normal tissue voxels; however, XDD demonstrated improved specificity in 2 out of 3 of the surgical tasks investigated (a slight reduction in specificity observed for the ethmoidectomy case). Small areas of failure for the XDD registration are evident in some cases at the edges of the excision area due to slight under-estimation of the excision volume. As in the phantom and simulation studies, the cadaver results suggest the greatest improvement in registration accuracy for XDD over conventional Demons registration for the larger excision volumes.

Discussion and Conclusions

The results presented in these examples indicate that conventional Demons registration is prone to erroneous distortion of registered images in the presence of excisions, and registration accuracy degrades in the area local to the site of the excision, which is the area where increased registration accuracy may be most needed. Explicit modeling of tissue excision implemented in the XDD registration approach resolved such effects to a significant degree. XDD largely removed excision-induced distortion about the site of the excision while maintaining the same level of registration accuracy as conventional Demons registration in regions far from the excision site.

Initial implementation of the XDD method involved simultaneous registration and excision segmentation using a simple thresholds of air-tissue intensity interfaces. Such an approach has advantages of simplicity and computational efficiency, but may be more difficult to optimize for more complex resections (e.g., tissue-in-tissue resection) as well as weighing tradeoffs between false-positive ejection (i.e., normal tissue erroneously ejected from the volume) versus true-negative deformation (i.e., normal tissue properly deformed within three-space). Incorporation of a simple surgical plan (e.g., a large Gaussian cloud marking an additional probability of excision) reduced distal, erroneous "salt-and-pepper" excision and makes reasonable use of prior information without additional computational burden.

Analogous to the missing-tissue problem investigated above is the question: what if the fixed and moving images differ in the physical addition of tissue (or other material)? In IGS, for example, the fixed image (intraoperative CBCT) may contain an interventional device (e.g., needle) not present in the moving (preoperative CT) image. The addition of an extra dimension from which material (i.e., signal intensity) may be introduced to the moving image at voxel locations identified as regions of mismatch according to another embodiment of the current invention.

Accurate account of tissue excision is an important aspect of deformable registration in image-guided surgery. Initial implementation of a Demons variant modified to include extra dimensions in the deformation field provided an accurate means of ejecting voxels from the moving image while maintaining the overall (sub-voxel) accuracy of the conventional Demons approach. Application to preclinical (cadaver) studies of CBCT-guided head and neck/skull base surgery demonstrated a major improvement in registration accuracy under conditions of realistic excision tasks.

REFERENCES

1. Dawson L A, Jaffray D A. Advances in image-guided radiation therapy. J. Clin. Oncol. 2007; 25(8):938-946.
2. Lauritsch G, Boese J, Wigstrom L, Kemeth H, Fahrig R. Towards cardiac C-arm computed tomography. IEEE Trans Med Imaging. 2006; 25(7):922-934.
3. Schafer S, Nithiananthan S, Mirota D J, et al. Mobile C-arm cone-beam CT for guidance of spine surgery: image quality, radiation dose, and integration with interventional guidance. Med Phys. 2011; 38(8):4563-4574.
4. Santos E R G, Ledonio C G, Castro C A, Truong W H, Sembrano J N. The accuracy of intraoperative O-arm images for the assessment of pedicle screw postion. Spine. 2012; 37(2):E119-125.
5. Daly M J, Siewerdsen J H, Moseley D J, Jaffray D A, Irish J C. Intraoperative cone-beam CT for guidance of head and neck surgery: Assessment of dose and image quality using a C-arm prototype. Med Phys. 2006; 33(10):3767-80.
6. Bachar G, Siewerdsen J H, Daly M J, Jaffray D A, Irish J C. Image quality and localization accuracy in C-arm tomosynthesis-guided head and neck surgery. Med Phys. 2007; 34(12):4664-4677.
7. Bachar G, Barker E, Nithiananthan S, et al. Three-dimensional tomosynthesis and cone-beam computed tomography: an experimental study for fast, low-dose intraoperative imaging technology for guidance of sinus and skull base surgery. Laryngoscope. 2009; 119(3):434-441.
8. Balachandran R, Schurzig D, Fitzpatrick J M, Labadie R F. Evaluation of portable CT scanners for otologic image-guided surgery. Int J Comput Assist Radiol Surg. 2012; 7(2):315-321.
9. Thirion J. Fast non-rigid matching of 3D medical images. France: INRIA; 1995. Available at: http://hal.inria.fr/inria-00077268/en/. Accessed Feb. 12, 2009.
10. Thirion J P. Image matching as a diffusion process: an analogy with Maxwell's demons. Med Image Anal. 1998; 2(3):243-260.
11. Pennec X, Cachier P, Ayache N. Understanding the "Demon's Algorithm": 3D Non-rigid Registration by Gradient Descent. In: Proceedings of the Second International Conference on Medical Image Computing and Computer-Assisted Intervention. Springer-Verlag; 1999:597-605. Available at: http://portal.acm.org/citation.cfm?id=709761. Accessed Apr. 26, 2009.
12. Wang H, Dong L, O'Daniel J, et al. Validation of an accelerated "demons" algorithm for deformable image registration in radiation therapy. Phys Med Biol. 2005; 50(12):2887-2905.
13. Vercauteren T, Pennec X, Perchant A, Ayache N. Diffeomorphic demons: Efficient non-parametric image registration. NeuroImage. 2009; 45(1, Supplement 1):S61-S72.
14. Nithiananthan S, Brock K K, Irish J C, Siewerdsen J H. Deformable registration for intra-operative cone-beam CT guidance of head and neck surgery. In: Engineering in Medicine and Biology Society, 2008. EMBS 2008. 30th Annual International Conference of the IEEE.; 2008:3634-3637.
15. Nithiananthan S, Brock K K, Daly M J, et al. Demons deformable registration for CBCT-guided procedures in the head and neck: Convergence and accuracy. Med. Phys. 2009; 36(10):4755-4764.
16. Nithiananthan S, Schafer S, Uneri A, et al. Demons Deformable Registration of CT and Cone-Beam C T Using an Iterative Intensity Matching Approach. Medical Physics. 2011.
17. Miga M I, Roberts D W, Kennedy F E, et al. Modeling of retraction and resection for intraoperative updating of images. Neurosurgery. 2001; 49(1):75-84; discussion 84-5.
18. Periaswamy S, Farid H. Medical image registration with partial data. Med Image Anal. 2006; 10(3):452-464.
19. Risholm P, Samsett E, Talos I-F, Wells W. A non-rigid registration framework that accommodates resection and retraction. Inf Process Med Imaging. 2009; 21:447-458.
20. Risholm P, Samset E, Wells III W. Validation of a nonrigid registration framework that accommodates tissue resection. In: San Diego, Calif., USA; 2010:762319-762319-11. Available at: http://link.aip.org/link/PSISDG/v7623/i1/p762319/s1&Agg=doi. Accessed Jan. 24, 2011.
21. Jaffray D A, Siewerdsen J H. Cone-beam computed tomography with a flat-panel imager: initial performance characterization. Med Phys. 2000; 27(6):1311-1323.
22. Chan Y, Siewerdsen J H, Rafferty M A, et al. Cone-beam computed tomography on a mobile C-arm: novel intraoperative imaging technology for guidance of head and neck surgery. J Otolaryngol Head Neck Surg. 2008; 37(1):81-90.
23. Siewerdsen J H, Chan Y, Rafferty M A, et al. Cone-beam CT with a flat-panel detector on a mobile C-arm:

preclinical investigation in image-guided surgery of the head and neck. In: Medical Imaging 2005: Visualization, Image-Guided Procedures, and Display. Vol 5744. San Diego, Calif., USA: SPIE; 2005:789-797. Available at: http://link.aip.org/link/?PSI/5744/789/1. Accessed Feb. 10, 2009.

24. Sezgin M, Sankur B. Survey over image thresholding techniques and quantitative performance evaluation. J. Electron. Imaging. 2004; 13(1):146-168.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the scope of the invention, as appreciated by those skilled in the art in light of the above teachings. It is therefore to be understood that, within the scope of the claims and their equivalents, the invention may be practiced otherwise than as specifically described.

We claim:

1. A system for registering images comprising an image registration unit, said image registration unit comprising non-transitory executable code that, when executed by the registration unit, causes the registration unit to:
   receive first image data for a first image in an N-dimensional space;
   receive second image data for a second image in said N-dimensional space;
   calculate a field of update vectors that maps said first image into a moving image; and
   map said first image into said moving image using said field of update vectors such that said moving image more closely matches said second image,
   wherein said field of update vectors comprises a plurality of N+M dimensional update vectors, each update vector having N spatial components and M extra components,
   wherein N is a number greater than zero,
   wherein M is a number greater than zero, and
   wherein said M extra components of said plurality of update vectors identify portions of said first image that are assigned external values during said mapping said first image into said moving image.

2. A system according to claim 1, wherein said calculating and said mapping are repeated a plurality of times by said registration unit to iteratively improve matching of successive moving images to said second image.

3. A system according to claim 2, wherein said plurality of times is a predetermined number.

4. A system medium according to claim 2, wherein said plurality of times is determined based on a measure of change between successive iterations.

5. A system according to claim 1, wherein said portions of said first image that are assigned external values during said mapping into said moving image correspond to at least one of removal or addition of image portions to said first image relative to said second image.

6. A system according to claim 5, wherein said first image comprises an image of an object and said second image comprises an image of said object in which a section of said object is absent,
   wherein said portions of said first image that are assigned external values during said mapping into said moving image correspond to said section of said object that is absent in said second image.

7. A system according to claim 5, wherein said assigned external values during said mapping into said moving image correspond to an object introduced into said second image that was absent from said first image.

8. A system according to claim 6, wherein N=3 and M=1,
   wherein said first image comprises an image of tissue,
   wherein said second image comprises said image of said tissue that has a portion excised, and
   wherein said portions of said first image that are assigned external values during said mapping into said moving image are assigned background image values corresponding to absence of tissue to correspond to said portion excised.

9. A system according to claim 1, wherein said M extra components of said update vectors are assigned values based on a probability that an external value is to be assigned during said mapping said first image into said moving image.

10. A system according to claim 9, wherein said probability comprises a weighting factor to weight some of said plurality of update vectors more strongly for assigning said external value than other of said plurality of update vectors.

11. A system according to claim 8, wherein said M=1 extra component of said update vectors utilize an overlap probability function given by $$P_{excision}(x) = P_{moving}^{tissue}(x) \cdot P_{fixed}^{air}(x)$$

wherein $$P_{moving}^{tissue}(x) = \text{sigm}(I_0(x), \alpha, T)$$

$$P_{fixed}^{air}(x) = \text{sigm}(I_1(x), -\alpha, T)$$

wherein $$\text{sigm}(I, \alpha, T) = \frac{1}{1 + e^{-\alpha(I-T)}}$$

wherein $I_0(x)$ is image intensity in said first image at x, $I_1(x)$ is image intensity in said second image at x, and wherein $\alpha$ and T are selectable parameters.

12. A system according to claim 11, wherein said update vectors are given by three spatial components as $$\vec{u}(x)_{1:3} = (1 - P_{excision}(x)) \cdot \vec{u}(x)$$

and fourth extra component as $$\vec{u}(x)_4 = P_{excision}(x) \cdot k_{force} \cdot a_{vox},$$

wherein $$\vec{u}(x) = \frac{2[I_0(x) - I_1(x)][\vec{\nabla} I_0(x) + \vec{\nabla} I_1(x)]}{K[I_0(x) - I_1(x)]^2 + \|\vec{\nabla} I_0(x) + \vec{\nabla} I_1(x)\|^2},$$

and wherein $a_{vox}$ is a selectable voxel size, K is a normalization factor, and $k_{force}$ and is a selectable parameter.

13. A system according to claim 8, wherein said M=1 extra component of said update vectors utilize an overlap probability function given by $$P^{excision(x)} = P_{moving}^{tissue}(x) \cdot P_{plan}(x)$$

wherein $$P_{moviong}^{tissue}(x) = \text{sigm}(x), \alpha, T)$$

$$P_{fixed}^{air}(x) = \text{sigm}(I_1(x), -\alpha, T)$$

wherein $$sigm(I, \alpha, T) = \frac{1}{1+e^{-\alpha(I-T)}}$$

wherein $I_0(x)$ is image intensity in said first image at x, $I_1(x)$ is image intensity in said second image at x, wherein $\alpha$ and T are selectable parameters, and $P_{plan}(x)$ is a long-range Gaussian cloud with peak value 1.0 centered substantially on an expected excision site.

14. A system according to claim 13, wherein said update vectors are given by three spatial components as $$\vec{u}(x)_{1:3} = (1-P_{excision}(x)) \cdot \vec{u}(x)$$

and fourth extra component as $$\vec{u}(x)_4 = P_{excision}(x) \cdot k_{force} \cdot a_{vox},$$

wherein $$\vec{u}(x) = \frac{2[I_0(x)-I_1(x)][\vec{\nabla}I_0(x)+\vec{\nabla}I_1(x)]}{K[I_0(x)-I_1(x)]^2 + \left\|\vec{\nabla}I_0(x)+\vec{\nabla}I_1(x)\right\|^2},$$

and wherein $a_{vox}$ is a selectable voxel size, K is a normalization factor, and $k_{force}$ and is a selectable parameter.

15. A method of registering images using an image registration unit, said image registration unit comprising non-transitory executable code that, when executed by the registration unit, causes the registration unit to perform the method, comprising;
  receiving first image data for a first image in an N-dimensional space;
  receiving second image data for a second image in said N-dimensional space;
  calculating a field of update vectors that maps said first image into a moving image; and
  mapping said first image into said moving image using said field of update vectors such that said moving image more closely matches said second image,
  wherein said field of update vectors comprises a plurality of N+M dimensional update vectors, each update vector having N spatial components and M extra components,
  wherein N is an integer greater than zero,
  wherein M is an integer greater than zero, and
  wherein said M extra components of said plurality of update vectors identify portions of said first image that are assigned external values during said mapping said first image into said moving image.

16. A method of registering images according to claim 15, wherein said calculating and said mapping are repeated a plurality of times to iteratively improve matching of successive moving images to said second image.

17. A method of registering images according to claim 16, wherein said plurality of times is a predetermined number.

18. A method of registering images according to claim 16, wherein said plurality of times is determined based on a measure of change between successive iterations.

19. A method of registering images according to claim 15, wherein said portions of said first image that are assigned external values during said mapping into said moving image correspond to at least one of removal or addition of image portions to said first image relative to said second image.

20. A method of registering images according to claim 19, wherein said first image comprises an image of an object and said second image comprises an image of said object in which a section of said object is absent,
  wherein said portions of said first image that are assigned external values during said mapping into said moving image correspond to said section of said object that is absent in said second image.

21. A method of registering images according to claim 19, wherein said assigned external values during said mapping into said moving image correspond to an object introduced into said second image that was absent from said first image.

22. A method of registering images according to claim 20, wherein N=3 and M=1,
  wherein said first image comprises an image of tissue,
  wherein said second image comprises said image of said tissue that has a portion excised, and
  wherein said portions of said first image that are assigned external values during said mapping into said moving image are assigned background image values corresponding to absence of tissue to correspond to said portion excised.

23. A method of registering images according to claim 15, wherein said M extra components of said update vectors are assigned values based on a probability that an external value is to be assigned during said mapping said first image into said moving image.

24. A method of registering images according to claim 23, wherein said probability comprises a weighting factor to weight some of said plurality of update vectors more strongly for assigning said external value than other of said plurality of update vectors.

25. A method of registering images according to claim 22, wherein said M=1 extra component of said update vectors utilize an overlap probability function given by $$P_{excision}(x) = P_{moving}^{tissue}(x) \cdot P_{fixed}^{air}(x)$$

wherein $$P_{moving}^{tissue}(x) = sigm(I_0(x), \alpha, T)$$

$$P_{fixed}^{air}(x) = sigm(I_1(x), -\alpha, T)$$

wherein $$sigm(I, \alpha, T) = \frac{1}{1+e^{-\alpha(I-T)}}$$

wherein $I_0(x)$ is image intensity in said first image at x, $I_1(x)$ is image intensity in said second image at x, and wherein $\alpha$ and T are selectable parameters.

26. A method of registering images according to claim 25, wherein said update vectors are given by three spatial components as $$\vec{u}(x)_{1:3} = (1-P_{excision}(x)) \cdot \vec{u}(x)$$

and fourth extra component as $$\vec{u}(x)_4 = P_{excision}(x) \cdot k_{force} \cdot a_{vox},$$

wherein $$\vec{u}(x) = \frac{2[I_0(x)-I_1(x)][\vec{\nabla}I_0(x)+\vec{\nabla}I_1(x)]}{K[I_0(x)-I_1(x)]^2 + \left\|\vec{\nabla}I_0(x)+\vec{\nabla}I_1(x)\right\|^2},$$

and wherein $a_{vox}$ is a selectable voxel size, and $k_{force}$ and K are selectable parameters.

27. A method of registering images according to claim 22, wherein said M=1 extra component of said update vectors utilize an overlap probability function given by $$P_{excision}(x) = P_{moving}^{tissue}(x) \cdot P_{plan}(x)$$

wherein $$P_{moving}^{tissue}(x) = \text{sigm}(I_0(x), \alpha, T)$$

$$P_{fixed}^{air}(x) \text{sigm}(I_1(x), -\alpha, T)$$

wherein $$\text{sigm}(I, \alpha, T) = \frac{1}{1 + e^{-\alpha(I-T)}}$$

wherein $I_0(x)$ is image intensity in said first image at x, $I_1(x)$ is image intensity in said second image at x, wherein $\alpha$ and T are selectable parameters, and $P_{plan}(x)$ is a long-range Gaussian cloud with peak value 1.0 centered substantially on an expected excision site.

28. A method of registering images according to claim 27, wherein said update vectors are given by three spatial components as $$\vec{u}(x)_{1:3} = (1 - P_{excision}(x)) \cdot \vec{u}(x)$$

and fourth extra component as $$\vec{u}(x)_4 = P_{excision}(x) \cdot k_{force} \cdot a_{vox}$$

wherein $$\vec{u}(x) = \frac{2[I_0(x) - I_1(x)][\vec{\nabla} I_0(x) + \vec{\nabla} I_1(x)]}{K[I_0(x) - I_1(x)]^2 + \|\vec{\nabla} I_0(x) + \vec{\nabla} I_1(x)\|^2},$$

and wherein $a_{vox}$ is a selectable voxel size, and $k_{force}$ and K are selectable parameters.

29. A computer-readable medium comprising non-transitory computer-executable code for registering images, said non-transitory computer-executable code comprising instructions that, when retrieved from a non-transitory computer-readable storage medium and executed by a computer, causes said computer to:
receive first image data for a first image in an N-dimensional space;
receive second image data for a second image in said N-dimensional space;
calculate a field of update vectors that maps said first image into a moving image; and
map said first image into said moving image using said field of update vectors such that said moving image more closely matches said second image,
wherein said field of update vectors comprises a plurality of N+M dimensional update vectors, each update vector having N spatial components and M extra components,
wherein N is an integer greater than zero,
wherein M is an integer greater than zero, and
wherein said M extra components of said plurality of update vectors identify portions of said first image that are assigned external values during said mapping said first image into said moving image.

30. A computer-readable medium according to claim 29, wherein said calculating and said mapping are repeated a plurality of times by said computer to iteratively improve matching of successive moving images to said second image.

31. A computer-readable medium according to claim 30, wherein said plurality of times is a predetermined number.

32. A computer-readable medium according to claim 30, wherein said plurality of times is determined based on a measure of change between successive iterations.

33. A computer-readable medium according to claim 29, wherein said portions of said first image that are assigned external values during said mapping into said moving image correspond to at least one of removal or addition of image portions to said first image relative to said second image.

34. A computer-readable medium according to claim 33, wherein said first image comprises an image of an object and said second image comprises an image of said object in which a section of said object is absent,
wherein said portions of said first image that are assigned external values during said mapping into said moving image correspond to said section of said object that is absent in said second image.

35. A computer-readable medium according to claim 33, wherein said assigned external values during said mapping into said moving image correspond to an object introduced into said second image that was absent from said first image.

36. A computer-readable medium according to claim 34, wherein N=3 and M=1,
wherein said first image comprises an image of tissue,
wherein said second image comprises said image of said tissue that has a portion excised, and
wherein said portions of said first image that are assigned external values during said mapping into said moving image are assigned background image values corresponding to absence of tissue to correspond to said portion excised.

37. A computer-readable medium according to claim 29, wherein said M extra components of said update vectors are assigned values based on a probability that an external value is to be assigned during said mapping said first image into said moving image.

38. A computer-readable medium according to claim 37, wherein said probability comprises a weighting factor to weight some of said plurality of update vectors more strongly for assigning said external value than other of said plurality of update vectors.

39. A computer-readable medium according to claim 36, wherein said M=1 extra component of said update vectors utilize an overlap probability function given by $$P_{excision}(x) = P_{moving}^{tissue}(x) \cdot P_{fixed}^{air}(x)$$

wherein $$P_{moving}^{tissue}(x) = \text{sigm}(I_0(x), \alpha, T)$$

$$P_{fixed}^{air}(x) = \text{sigm}(I_1(x), -\alpha, T)$$

wherein $$\text{sigm}(I, \alpha, T) = \frac{1}{1 + e^{-\alpha(I-T)}}$$

wherein $I_0(x)$ is image intensity in said first image at x, $I_1(x)$ is image intensity in said second image at x, and wherein $\alpha$ and T are selectable parameters.

40. A computer-readable medium according to claim 39, wherein said update vectors are given by three spatial components as $$\vec{u}(x)_{1:3} = (1 - P_{excision}(x)) \cdot \vec{u}(x)$$

and fourth extra component as $$\vec{u}(x)_4 = P_{exercision}(x) \cdot k_{force} \cdot a_{vox}$$

wherein $$\vec{u}(x) = \frac{2[I_0(x) - I_1(x)][\vec{\nabla} I_0(x) + \vec{\nabla} I_1(x)]}{K[I_0(x) - I_1(x)]^2 + \|\vec{\nabla} I_0(x) + \vec{\nabla} I_1(x)\|^2},$$

and
wherein $a_{vox}$ is a selectable voxel size, and $k_{force}$ and K are selectable parameters.

41. A computer-readable medium according to claim 36, wherein said M=1 extra component of said update vectors utilize an overlap probability function given by $$P_{excision}(x) = P_{moving}{}^{tissue}(x) \cdot P_{fixed}{}^{air}(x) \cdot P_{plan}(x)$$

wherein $$P_{moving}{}^{tissue}(x) = sigm(I_0(x), \alpha, T)$$

$$P_{fixed}{}^{air}(x) = sigm(I_1(x), -\alpha, T)$$

wherein $$sigm(I, \alpha, T) = \frac{1}{1 + e^{-\alpha(I-T)}}$$

wherein $I_0(x)$ is image intensity in said first image at x, $I_1(x)$ is image intensity in said second image at x, wherein $\alpha$ and T are selectable parameters, and
$P_{plan}(x)$ is a long-range Gaussian cloud with peak value 1.0 centered substantially on an expected excision site.

42. A computer-readable medium according to claim 41, wherein said update vectors are given by three spatial components as $$\vec{u}(x)_{1:3} = (1 - P_{excision(X)}) \cdot \vec{U}_{(x)}$$

and fourth extra component as $$\vec{u}(x)_4 = P_{excision}(x) \cdot k_{force} \cdot a_{vox},$$

wherein $$\vec{u}(x) = \frac{2[I_0(x) - I_1(x)][\vec{\nabla} I_0(x) + \vec{\nabla} I_1(x)]}{K[I_0(x) - I_1(x)]^2 + \|\vec{\nabla} I_0(x) + \vec{\nabla} I_1(x)\|^2},$$

and
wherein $a_{vox}$ is a selectable voxel size, and $k_{force}$ and K are selectable parameters.

* * * * *